US010610890B2

(12) United States Patent
Hasegawa et al.

(10) Patent No.: US 10,610,890 B2
(45) Date of Patent: Apr. 7, 2020

(54) ULTRASONIC TRANSDUCER ELEMENT, METHOD OF MANUFACTURING THE SAME, AND ULTRASONIC IMAGE PICKUP DEVICE

(71) Applicant: HITACHI, LTD., Tokyo (JP)

(72) Inventors: Hiroaki Hasegawa, Tokyo (JP); Taiichi Takezaki, Tokyo (JP); Shuntaro Machida, Tokyo (JP); Daisuke Ryuzaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 296 days.

(21) Appl. No.: 15/579,383

(22) PCT Filed: Jun. 4, 2015

(86) PCT No.: PCT/JP2015/066236
§ 371 (c)(1),
(2) Date: Dec. 4, 2017

(87) PCT Pub. No.: WO2016/194208
PCT Pub. Date: Dec. 8, 2016

(65) Prior Publication Data
US 2018/0161813 A1    Jun. 14, 2018

(51) Int. Cl.
*B06B 1/02* (2006.01)
*H04R 31/00* (2006.01)
(Continued)

(52) U.S. Cl.
CPC .......... *B06B 1/0292* (2013.01); *B81B 3/0037* (2013.01); *H03H 9/24* (2013.01);
(Continued)

(58) Field of Classification Search
CPC ................ B06B 1/0292; B81B 3/0037; B81B 2201/0271; B81B 2207/053;
(Continued)

(56) References Cited

U.S. PATENT DOCUMENTS

2009/0140609 A1    6/2009  Huang
2009/0301200 A1   12/2009  Tanaka et al.
(Continued)

FOREIGN PATENT DOCUMENTS

| CN | 108886660 A  * | 11/2018 | ........... A61B 8/4483 |
| EP | 3306952 A4 * | 1/2019 | ............... H03H 9/24 |

(Continued)

OTHER PUBLICATIONS

International Search Report for WO 2016/194208 A1, dated Aug. 18, 2015.

*Primary Examiner* — Daniel Pihulic
(74) *Attorney, Agent, or Firm* — Volpe and Koenig, P.C.

(57) ABSTRACT

An ultrasonic transducer element includes a substrate, a lower electrode on a first surface of the substrate, a first insulating film on the lower electrode, a first cavity layer on the first insulating film, a second insulating film on the first cavity layer, an upper electrode on the second insulating film that overlaps the first cavity layer, a third insulating film on the upper electrode, a second cavity layer on the third insulating film, a fourth insulating film on the second cavity layer, a fixing portion formed by the second to fourth insulating films, a movable portion in a membrane insides the second cavity layer, a first connection portion and a second connection portion that are stacked with a gap and the connection portions are configured by the second to fourth insulating films connecting the movable portion and the fixing portion.

10 Claims, 21 Drawing Sheets

(51) Int. Cl.
     *H03H 9/24*    (2006.01)
     *H04R 19/00*   (2006.01)
     *B81B 3/00*    (2006.01)
     *H03H 9/17*    (2006.01)
     *A61B 8/00*    (2006.01)
     *G01N 29/24*   (2006.01)
(52) U.S. Cl.
     CPC ............ *H04R 19/00* (2013.01); *H04R 31/00*
             (2013.01); *A61B 8/4483* (2013.01); *B81B
             2201/0271* (2013.01); *B81B 2203/0315*
             (2013.01); *B81B 2207/053* (2013.01); *G01N
             29/2406* (2013.01); *H03H 9/174* (2013.01)
(58) Field of Classification Search
     CPC ............ B81B 2203/0315; H04R 19/00;
                     H04R 31/00; H03H 9/24; H03H 9/174;
                     G01N 29/2406; A61B 8/4483
     See application file for complete search history.

(56) References Cited

U.S. PATENT DOCUMENTS

2018/0161813 A1\* 6/2018 Hasegawa ................ H03H 9/24
2019/0118222 A1\* 4/2019 Hasegawa ............. B06B 1/0292

FOREIGN PATENT DOCUMENTS

| JP | 2006-319712 A | 11/2006 | |
|----|---------------|---------|---|
| JP | 2009-182838 A | 8/2009 | |
| JP | 2011-507561 A | 3/2011 | |
| JP | 2012-004926 A | 1/2012 | |
| WO | 2007/046180 A1 | 4/2007 | |
| WO | 2009/096576 A2 | 8/2009 | |
| WO | 2014/103334 A1 | 7/2014 | |
| WO | WO-2016194208 A1 \* | 12/2016 | ............... H03H 9/24 |
| WO | WO-2018061395 A1 \* | 4/2018 | ........... B06B 1/0292 |

\* cited by examiner (a) B-B' CROSS-SECTION (b)

(a) A-A' CROSS-SECTION (b) B-B' CROSS-SECTION (a)

(b)

(a)

(b)

(a)

(b)

(a)

(b)

(a)

(b)

(a)

(b)

(a)

(b)

(a)

(b)

(a)

(b)

(a)

(b)

(a) D-D' CROSS-SECTION (b)

(a) C-C' CROSS-SECTION (b) D-D' CROSS-SECTION (a) F-F' CROSS-SECTION (b)

(a) E-E' CROSS-SECTION (b) F-F' CROSS-SECTION

ULTRASONIC TRANSDUCER ELEMENT, METHOD OF MANUFACTURING THE SAME, AND ULTRASONIC IMAGE PICKUP DEVICE

TECHNICAL FIELD

The present invention relates to a manufacturing technology of an ultrasonic transducer element, and particularly to a structure of the ultrasonic transducer element manufactured by a MEMS (Micro Electro Mechanical System) technique, and a technology which is effectively applied to the manufacturing method.

BACKGROUND ART

An ultrasonic transducer is assembled in an ultrasonic probe of an ultrasonic image pickup device to transmit/receive ultrasonic waves, and used in various usages such as diagnosis of tumors in human bodies and inspection of cracks generated in buildings.

The ultrasonic transducer equipped with a piezoelectric material has been used so far. In recent years, with the progress of MEMS technologies, a capacitive micromachined ultrasonic transducer (CMUT) is being actively developed for the commercialization in which a vibration portion is formed on a silicon substrate. The CMUT has advantages of a wide frequency range of available ultrasonic waves and of high sensitivity compared to the ultrasonic transducer equipped with the conventional piezoelectric material. In addition, since a technique of processing an LSI is used in the manufacturing, it is possible to perform micromachining, and it is suitable for Manufacturing a vibrator for the ultrasonic probe.

As a related art, for example, PTLs 1 to 3 disclose a single CMUT element and a CMUT which is disposed in an array.

CITATION LIST

Patent Literature

PTL 1: JP 2006-319712 A
PTL 2: JP 2009-182838 A
PTL 3: JP 2012-004926 A

SUMMARY OF INVENTION

Technical Problem

A basic structure and operations of a CMUT element will be described using a model of FIG. 1. FIG. 1 illustrates a cross-sectional structure of the basic CMUT element.

A cavity layer (cavity portion) 102 is formed with being surrounded by insulating films 106, 103, and 107 in the upper layer of a lower electrode 101. The insulating film 106 is disposed with a gap with the lower electrode 101 and the cavity layer (cavity portion) 102, and a membrane 105 is configured by the insulating film 107 of the upper layer of the cavity layer 102 and an upper electrode 104.

The insulating film 107 in the membrane 105 is formed wider than the upper region of the cavity layer 102, and the insulating film 107 and the upper electrode 104 between the vertical tangent lines M and M' of both side surfaces of the cavity layer 102 in FIG. 1 are called the membrane 105 in this specification.

The insulating film 103 surrounding the side surface of the cavity layer 102 is configured by a plurality of insulating films, divided from the insulating film 107 of the membrane 105 with the vertical tangent lines M and M' as boundaries, and serves as a fixing portion which supports the vibration of the membrane 105.

When a DC voltage and an AC voltage are superimposed between the upper electrode 104 and the lower electrode 101, an electrostatic force works between the upper electrode 104 and the lower electrode 101, the membrane 105 vibrates by a frequency of the applied AC voltage, and the ultrasonic waves are generated. On the contrary, in the case of reception, the membrane 105 vibrates by a pressure of the ultrasonic wave reached the surface of the membrane 105. Then, since a distance between the upper electrode 104 and the lower electrode 101 changes, an electrostatic capacitance changes, and the ultrasonic wave can be detected.

As can be seen from the above operation principles, the pressure of the transmitting ultrasonic wave depends on a vibration amplitude of the membrane 105. The outer periphery of the membrane 105 is supported by the fixing portion (insulating film) 103, and the vibration amplitude is generated by a bending caused by an elastic deformation of the membrane. With this configuration, the vibration amplitude of the membrane 105 is continuously distributed such that the vibration amplitude becomes zero at the outer periphery and is maximized at the center. Therefore, even in the CMT in which the area viewed from the upper surface of the membrane is equal to the maximum amplitude, a generated sound pressure is different according to a distribution shape of the vibration amplitude. In other words, since the sound pressure is maximized in the vibration generated when an inflexible plate translates in a piston shape, it is desirable that the area where the vibration amplitude comes near the maximum amplitude is expanded. However, the outer periphery of the membrane is fixedly supported, and thus the membrane near the fixedly supported point cannot vibrate and does not contribute to transferring sound waves. In such a case, the maximum amplitude of the membrane may be increased in order to increase the pressure of the transferring ultrasonic wave. However, there is a need to increase a drive voltage to vibrate the membrane, and there is a possibility to cause a problem such as a dielectric breakdown of the insulating film interposed between upper and lower electrodes and charging-up of the insulating film due to charges supplied from the electrode to the insulating film during a period when the CMUT is used. When the insulating film is charged up, the electric field between the upper and lower electrodes is blocked by the charges electrified in the insulating film, and the driving may be not appropriately performed.

As a structure which increases the sound pressure of the transferring ultrasonic wave while suppressing an increase of the drive voltage, PTLs 1, 2, and 3 disclose structures in which the peripheral portion of the membrane 105 is easily deformed and the Center portion is hardly deformed in consideration of the above problems. As a method of easily deforming the ends of the membrane, PTL 1 employs a structure in which grooves are provided in the ends of the membrane, PTL 2 employs a structure in which a thickness of the center portion of the membrane is increased, and PTL 3 employs a structure in which the ends of the membrane are formed in a corrugate shape. However, about 50% of the area of the membrane can be efficiently used even if these methods are employed.

An object of the invention is to provide a structure and a method of manufacturing the structure in which an increase of a drive voltage in the CMUT can be suppressed and a transmission sound pressure of the ultrasonic wave of the CMUT can be increased by expanding the area which can be effectively used by making the vibration of the membrane approach a vibration of a piston shape.

Other objects and novel characteristics besides the above description of this invention will be apparent through the explanation and the accompanying drawings of this specification.

Solution to Problem

In order to solve the above problems, the invention provides an ultrasonic transducer element which is configured by a substrate, a lower electrode which is formed on a first principal surface of the substrate, a first insulating film which is formed on the lower electrode, a first cavity layer which is formed on the first insulating film, a second insulating film which is formed on the first cavity layer, an upper electrode which is formed on the second insulating film and disposed at a position overlapping with the first cavity layer when viewed from an upper surface, a third insulating film which is formed on the upper electrode, a second cavity layer which is formed on the third insulating film, a fourth insulating film which is formed on the second cavity layer, a fixing portion which is formed by the second to fourth insulating films surrounding an outer periphery of the first cavity layer when viewed from the upper surface of the first principal surface of the substrate, a movable portion which is a region inside the second cavity layer in a membrane which is formed by the second to fourth insulating films formed on the first cavity layer and the upper electrode, a first connection portion and a second connection portion which is stacked with a gap with the first connection portion, the connection portions being configured by the second to fourth insulating films connecting the movable portion and the fixing portion.

In addition, in the ultrasonic transducer element according to the invention in order to solve the above problems, the second cavity layer is configured between the first connection portion and the second connection portion.

In addition, in the ultrasonic transducer element according to the invention in order to solve the above problems, a material layer having an elastic modulus lower than the insulating film is formed on the third insulating film instead of the second cavity layer, the movable portion becomes a region inside the material layer having a low elastic modulus instead of the second cavity layer in the membrane, and the material layer having the low elastic modulus is included between the first connection portion and the second connection portion compared to both the connection portions.

In addition, in the ultrasonic transducer element according to the invention in order to solve the above problems, the second cavity layer or a material layer having a low elastic modulus compared to both the connection portions is disposed at a continuous position bordering an outer periphery of the first cavity layer and at a position overlapping with the first cavity layer when viewed from the upper surface of the first principal surface of the substrate.

In addition, in order to solve the above problems, the invention provides a method of manufacturing an ultrasonic transducer element which is formed in a first principal surface of a substrate, the method including: (a) forming a first electrode on the first principal surface of the substrate; (b) forming a first insulating film on the electrode; (c) forming a first sacrifice layer at a position overlapping with the first electrode on the first insulating film when viewed from an upper surface; (d) forming a second insulating film on the first sacrifice layer; (e) forming a second electrode at a position which is formed on the second insulating film and overlaps with the first sacrifice layer when viewed from the upper surface; (f) forming a third insulating film on the second electrode; (g) forming a second sacrifice layer on the third insulating film to be overlapped with an outer periphery of the first sacrifice layer; (h) forming a fourth insulating film on the second sacrifice layer and the third insulating film; (i) forming an opening which passes through the fourth insulating film, the second sacrifice layer, the third insulating film, and the second insulating film, and reaches the first sacrifice layer; (j) forming first and second cavity layers by removing the first and second sacrifice layers through the opening to form a first connection portion between the first cavity layer and the second cavity layer and a second connection portion in an upper portion of the second cavity layer; and (k) forming a fifth insulating film on the fourth insulating film to seal the opening.

Advantageous Effects of Invention

An effect obtained by a representative embodiment of the invention disclosed in the present application is as follows.

According to the invention, a movable portion of a membrane of a CMUT element is suppressed from being bent, and also it is possible to suppress a drive voltage from being increased and to increase a transmitting sound pressure of an ultrasonic wave by increasing a vibration area of the membrane.

DESCRIPTION OF EMBODIMENTS

Figure 1:
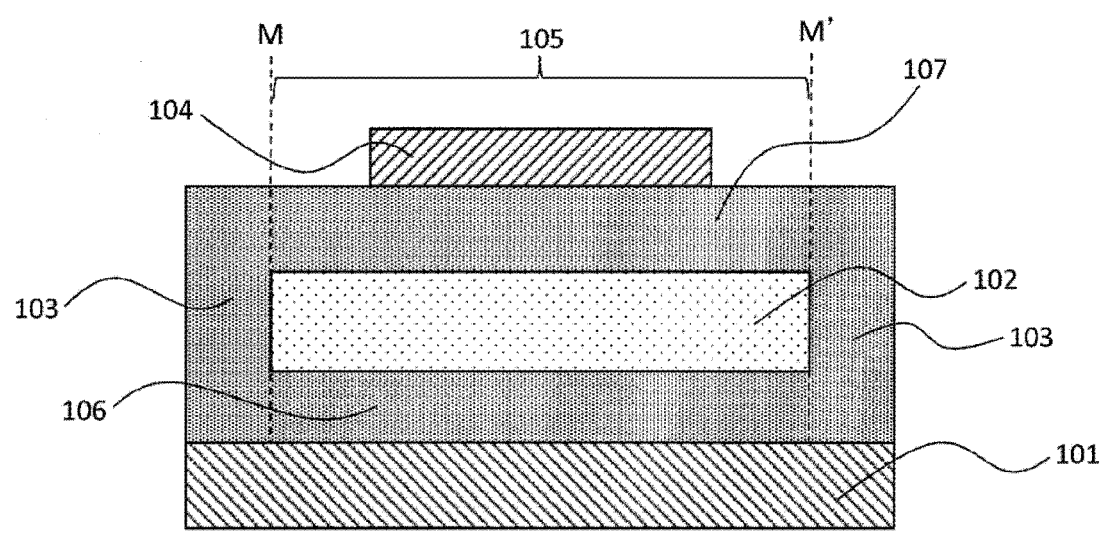
FIG. 1 is a cross-sectional view of a basic CMUT element.

In the following description of embodiments, in order to realize an object of manufacturing a CMUT which can suppress an increase of a drive voltage and expand a transmission sound pressure of the ultrasonic wave, a membrane and a fixing unit of the membrane are connected by a connection portion which is divided into two layers, and the membrane vibrates like a piston vibration while keeping flatness of the center portion of the membrane at the time of transmitting the ultrasonic wave.

Further, in the drawings for describing the following embodiments, the same members will be assigned with the same symbol in principle, and the redundant description will be omitted. In addition, the following embodiments will be described by being divided into several sections or examples if needed for the convenience of explanation, and these sections and examples are relevant to each other if not otherwise specified, and some or all of modification's, details, and additional explanations are relevant.

In addition, in a case where the numerical data (number, numerical value, amount, range, etc.) of elements is denoted in the following embodiments, the numerical data is not limited to the specified number, and may be equal to or more or less than the specified number if not otherwise specified and the numerical data is not apparently specified in principle. Further, in the following embodiments, it is a matter of course that the components (including elemental steps) are not necessarily essential if not otherwise specified and the components are not necessarily essential in principle.

Similarly, in the following embodiments, when it comes to denoting shapes and positional relations of the components, it is a matter of course that any shape may be included as long as it is substantially close or similar to that shape if not otherwise specified and not apparently considered as it is in principle. This is also the same in the numerical values and ranges. Further, some components may be hatched even in a top view in order to help understanding.

First Embodiment

FIG. 2(b) is a top view illustrating an inner configuration of an ultrasonic transducer (CMUT) element in a first embodiment in which an insulating film is removed and a profile of a cavity layer is depicted by a contour line. In the first embodiment of the invention, the profile of a first cavity layer 102 immediately below the membrane viewed from the upper surface is a rectangular shape. Further, a second cavity layer is disposed in a cylinder region of which the cross-section is a rectangular shape continuous in a rectangular frame when viewed from the upper surface as if bordering the outer periphery of the membrane of the upper portion of the first cavity layer.

FIG. 2(a) illustrates a cross-sectional view taken along line B-B' in FIG. 2(b). An example of a positional relation between a lower electrode 101, an upper electrode 104, and the first and second Cavity layers 102 and 305 on a substrate 301 is illustrated.

A CMUT element in the first embodiment is configured by a layer-stacked structure of the lower electrode 101 formed on the substrate 301, the first cavity layer 102, the second cavity layer 305 surrounded by contour lines 204 and 205 illustrated in a broken line in FIG. 2(b), and the upper electrode 104. In addition, while being formed to cover the substrate, the respective electrodes, and the respective cavity layers, the insulating film is not illustrated in order to illustrate the structure of the lower layers of the respective insulating films. A wet etching hole 201 is used to form the cavity layer, and protrusions are provided in the first and second cavity layers to be connected to the hole. Pad openings 202 and 203 are formed to apply a voltage to the respective electrodes.

FIG. 3(a) is a cross-sectional view taken along line A-A' of FIG. 2(b). FIG. 3(b) is a cross-sectional view taken along line B-B' of FIG. 2(b). In FIGS. 3(a) and 3(b), the lower electrode 101 is formed on an insulating film 1031 formed in the substrate 301, as illustrating the CMUT element including the insulating film. The cavity layer 102 is formed in the upper layer of the lower electrode 101 through an insulating film 1032. An insulating film 1033 is formed to surround the cavity portion 102, and the upper electrode 104 is formed in the upper layer of the insulating film 1033. In the upper layer of the upper electrode 104, the second cavity layer 305 is formed through an insulating film 1034, an insulating film 1035 is formed to surround the second cavity layer 305 and the insulating film 1034, and an insulating film 1036 is formed in the upper layer of the insulating film 1035.

In addition, the wet etching hole 201 is formed in the insulating films 1035, 1034, and 1033 to pass through these films. The wet etching hole 201 is formed to form the cavity layers 102 and 305, and buried with an insulating film 1036 after the cavity layer is formed. The pad openings 202 and 203 are formed to supply a voltage to the lower electrode 101 and the upper electrode 104, respectively.

In FIGS. 2(a) and 2(b) and FIGS. 3(a) and 3(b), the membrane is configured by the insulating films 1033 to 1036 in a region of the upper portion of the first cavity layer 102 and the upper electrode 104. When the membrane vibrates at the time of transceiving an ultrasonic wave, a movable portion is defined as a region which is recognized to have an amplitude equal to or more than a predetermined ratio with respect to a maximum amplitude. The movable portion in the first embodiment is within a rectangular region surrounded by the contour line 204 inside the second cavity layer 305 in FIG. 2(b).

In addition, in the first embodiment, the contour line 205 outside the second cavity layer 305 is substantially matched to the Contour of the first cavity layer 102. Therefore, the movable portion of the membrane is configured by a fixing portion made of the insulting film surrounding the side surface of the first cavity layer 102, and a connection portion through which the insulating films above and below the region of the second cavity layer surrounded by the contour line 204 and the contour line 205 in FIG. 2(b) connect the movable portion and the fixing portion. The connection portion is elastically deformed to cause the movable portion to vibrate so as to generate the ultrasonic wave.

The feature of the first embodiment is in that a movable portion 304 of the membrane inside the contour line 204 when viewed from the upper surface of the substrate is connected to a fixing portion 302 outside the contour line 205 by a first connection portion 3031 and a second connection portion 3032 as illustrated in FIGS. 2(a) and 2(b) and FIGS. 3(a) and 3(b). The first connection portion 3031 and the second connection portion 3032 are stacked with a gap from the second cavity layer 305.

The effect obtained by stacking the connection portion is as follows. FIG. 4 is a graph illustrating a bending curve of the insulating film 1033 along the cross-section taken along line A-A' of FIG. 2 when the drive voltage is applied to the ultrasonic transducer element having the structure of FIGS. 2 and 3 to vibrate. A curve 401 shows the first element, and a curve 402 shows a bending amount of the conventional ultrasonic transducer element illustrated in FIG. 1 in which the second connection portion 3032 is not provided. Both ends N and N' of the graph correspond to the ends of both side surfaces of the first cavity layer 102 illustrated in FIGS. 2(b) and 3(a). It can be seen from the comparison between the curves 401 and 402 that the bending shape in the first embodiment is flatter in a region corresponding to the movable portion 304 between both the side surfaces having the same maximum bending amount.

The function of the second connection portion 3032 is as follows. When the bending occurs by an electrostatic force, a tension force is generated in an engaging portion with the movable portion 304 by extension of the connection portion 3032. As a result, a bending moment is generated in a direction bending the membrane 105 back, and a bending 403 is generated along the contour line 204 surrounding the movable portion 304. As a result, the bending of the center portion of the movable portion 304 can be suppressed, and it is possible to increase a vibration area having a vibration ratio equal to or more than a predetermined ratio with respect to a maximum amplitude of the membrane.

In FIG. 3(a), for more explanation, a parallel link mechanism is configured by the first connection portion 3031, the second Connection portion 3032, the movable portion 304, and the fixing portion 302 with the second cavity layer interposed therebetween, and a pulling-up force preventing the center portion of the movable portion from being dented in a parabolic shape is shared by two connection portions even when the movable portion of the membrane is displaced in a vertical direction. Therefore, the displacement is changed from a parabolic shape 402 to a bathtub shape 401 as illustrated in FIG. 4.

Further, FIGS. 2(a) and 2(b) illustrate an example that the contour line 205 of the outer periphery of the second cavity layer 305 is substantially matched to the contour of the profile of the first cavity layer 102. However, there is no need to match these contours, the contour line may be positioned outside or inside as long as it is disposed in the vicinity of the contour of the profile of the first cavity layer 102. A position of the boundary between the fixing portion 302 and the connection portion is changed by the position of the contour line 205.

In this case, the contour line 204 of the inner periphery of the second cavity layer 305 is needed to be positioned inside the contour of the profile of the first cavity layer 102 when viewed from the upper surface of the first cavity layer 102.

Next, a method of manufacturing the CMUT element described in the first embodiment will be described using the drawings. FIGS. 5(a) to 15(a) illustrate cross-sectional views taken along line A-A' in FIG. 2(b), and FIGS. 5(b) to 15(b) illustrate cross-sectional views taken along line B-B' in FIG. 2(b).

First, as illustrated in FIGS. 5(a) and 5(b), the insulating film 1031 made of a silicon oxide film is formed on the substrate 301 by 500 nm, and then the lower electrode 101 made of an aluminum alloy film is formed by 100 nm. Then, the insulating film 1032 made of a silicon oxide film is deposited on the lower electrode 101 by 200 nm using a plasma CVD (Chemical Vapor Deposition) method.

Next, as illustrated in FIGS. 6(a) and 6(b), a sacrifice layer 501 made of a polycrystalline silicon film is deposited in the upper surface of the insulating film 1032 made of a silicon oxide film by 300 nm using the plasma CVD method. Then, the sacrifice layer 501 made of a polycrystalline silicon film is formed using a photolithography technique and a dry etching technique. The remaining portion will be the first cavity layer 102 in the following procedure.

Subsequently, as illustrated in FIGS. 7(a) and 7(b), the insulating film 1033 made of a silicon oxide film is deposited by 200 nm to cover the sacrifice layer 501 and the insulating film 1032 made of a silicon oxide film using the plasma CVD method.

Next, as illustrated in FIGS. 8(a) and 8(b), an aluminum alloy film is deposited by 100 nm using a sputtering method in order to form the upper electrode 104. Then, the upper electrode 104 is formed using the photolithography technique and the dry etching technique, and subsequently, as illustrated in FIGS. 9(a) and 9(b), the insulating film 1034 made of a silicon oxide film is deposited by 200 nm using the plasma CVD method so as to cover the upper electrode 104 and the insulating film 1033 made of a silicon oxide film.

Figure 2:
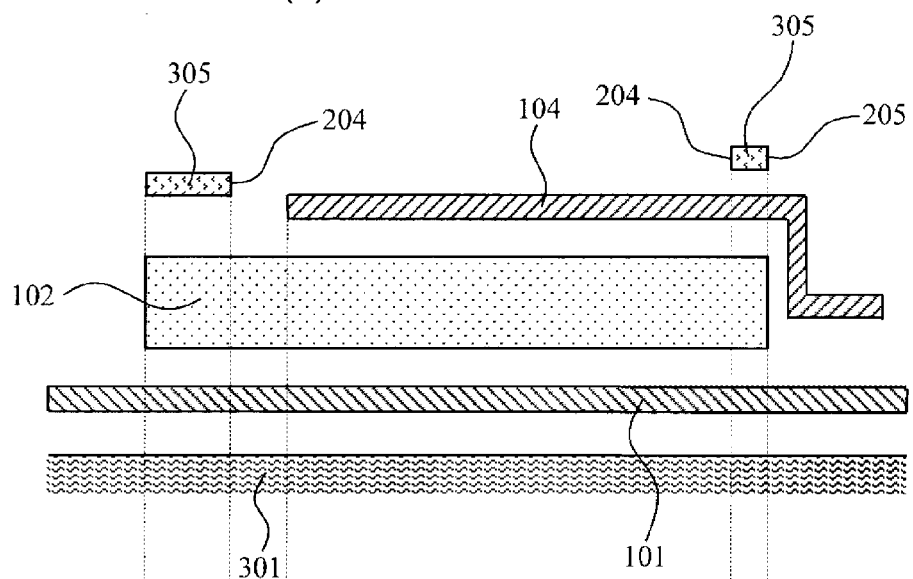
FIG. 2(a) is a cross-sectional view of the CMUT element in a first embodiment of the invention excepting an insulating film.
FIG. 2(b) is a top view when viewed from the upper surface of a substrate.
Figure 2:
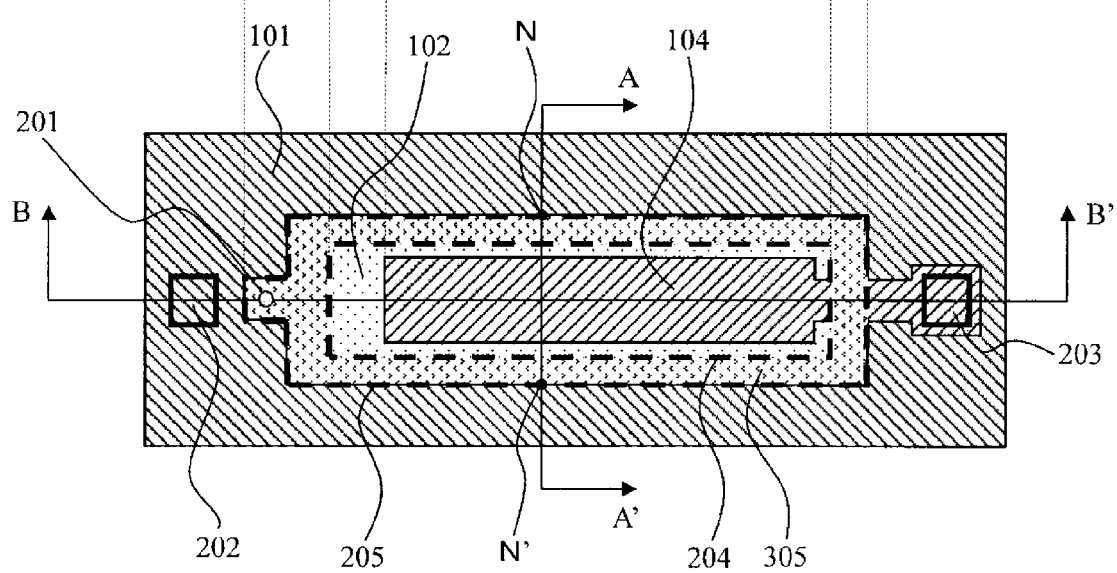

Next, as illustrated in FIGS. 10(a) and 10(b), a sacrifice layer 901 made of a polycrystalline silicon film is deposited in the upper surface of the insulating film 1034 made of a silicon oxide film by 200 nm using the plasma CVD method. Then, the sacrifice layer 901 made of a polycrystalline silicon film is formed using the photolithography technique and the dry etching technique. As illustrated in FIG. 2, the sacrifice layer 901 is formed on the insulating film 1034 in a cylinder shape which is continuous in a rectangular shape when viewed from the upper surface. The remaining portion will be the second cavity layer 305 in the following procedure.

Then, as illustrated in FIGS. 11(a) and 11(b), the insulating film 1035 made of a silicon oxide film is deposited by 200 nm using the plasma CVD method so as to cover the sacrifice layer 901 and the insulating film 1034 made of a silicon oxide film.

Subsequently, as illustrated in FIGS. 12(a) and 12(b), the wet etching hole 201 reaching the sacrifice layer 501 is formed in the insulating films 1035, 1034, and 1033 made of a silicon oxide film and the sacrifice layer 901 interposed by these insulating films using the photolithography technique and the dry etching technique.

Thereafter, as illustrated in FIGS. 13(a) and 13(b), the sacrifice layers 901 and 501 are subjected to the wet etching using potassium hydroxide through the wet etching hole 201, so as to form the cavity layers 305 and 102.

Next, as illustrated in FIGS. 14(a) and 14(b), the wet etching hole 201 is buried, and an insulating film 1036 made of a silicon nitride film is deposited by 100 nm using the plasma CVD method in order to seal the cavity layers 305 and 102.

Then, as illustrated in FIGS. 15(a) and 15(b), the pad openings 202 and 203 are formed using the photolithography technique and the dry etching technique to pass through the insulating films 1036, 1035, 1034, 1033, and 1032 made of a silicon oxide film, and reach the lower electrode 101 and the upper electrode 104. As described above, the CMUT element in the first embodiment can be formed.

Further, the CMUT element in FIG. 2(b) has been illustrated to have the first cavity layer in a rectangular shape when viewed from the upper surface of the substrate, but the shape is not limited thereto, and may be a circle or a polygon for example.

The materials of the CMUT element illustrated in the first embodiment are given as an examplary combination, and tungsten or other conductive materials may be used as the materials of the upper and lower electrodes. In addition, there is no need to use the same material as the material of the insulating film. For example, in the first embodiment, only the film of the uppermost layer of the connection portion 3032 is made of a silicon nitride film in order to avoid infiltration of moisture into the inner structure, but other insulating film may be used. In such a case, both film thicknesses may be adjusted to control the rigidity of the connection portions 3031 and 3032 to avoid unbalance in the rigidity of the connection portions 3031 and 3032. Any material may be used for the sacrifice layer as long as a wet etching selectivity with respect to the material surrounding the sacrifice layer is secured. Therefore, an SOG film (Spin-on-Glass) or a metal film may be used besides the polycrystalline silicon film.

Second Embodiment

Figure 16:
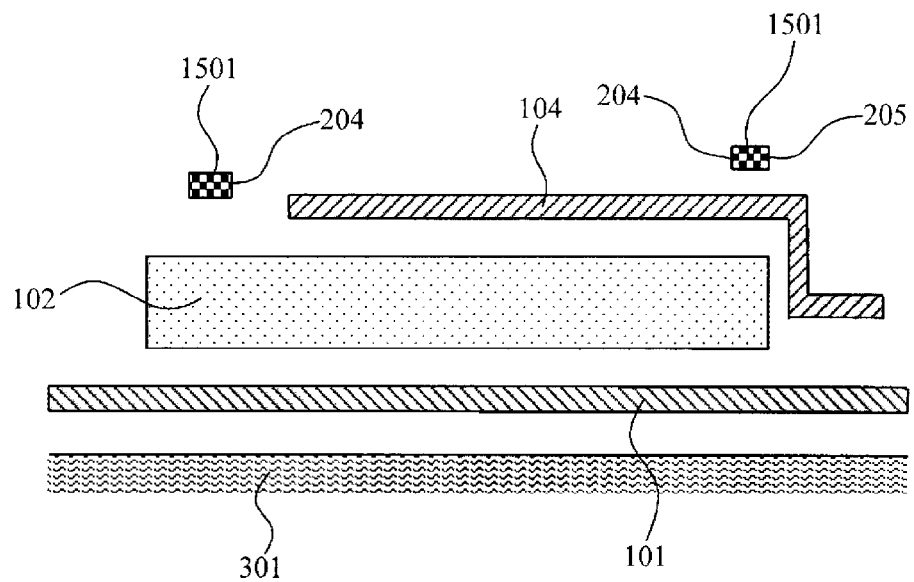
FIG. 16(a) is a cross-sectional view illustrating a CMUT element in a second embodiment of the invention excepting an insulating film.
FIG. 16(b) is a top view when viewed from the upper surface of the substrate.
Figure 16:
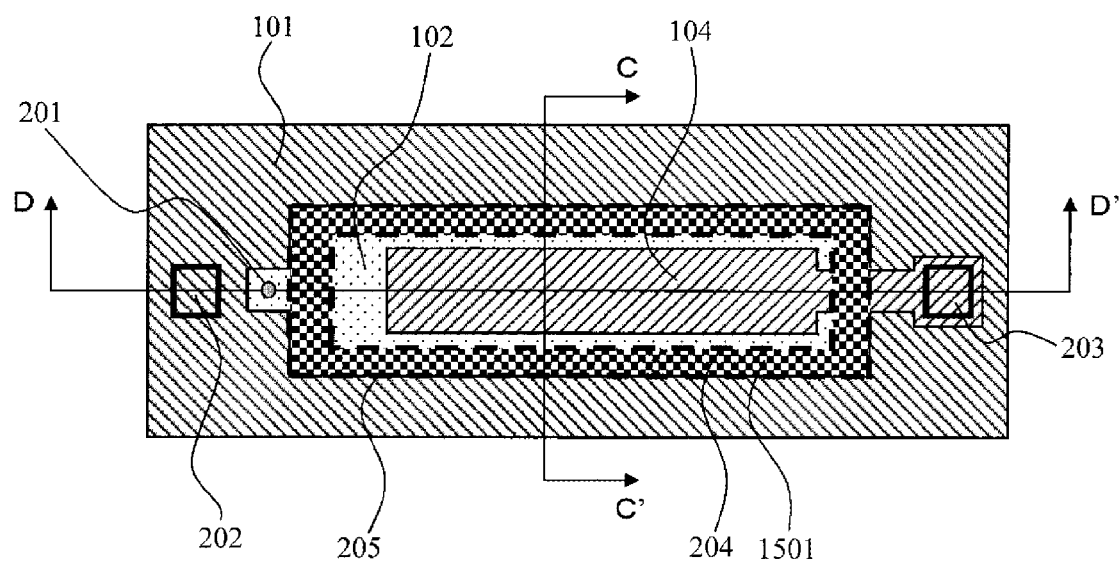
Figure 17:
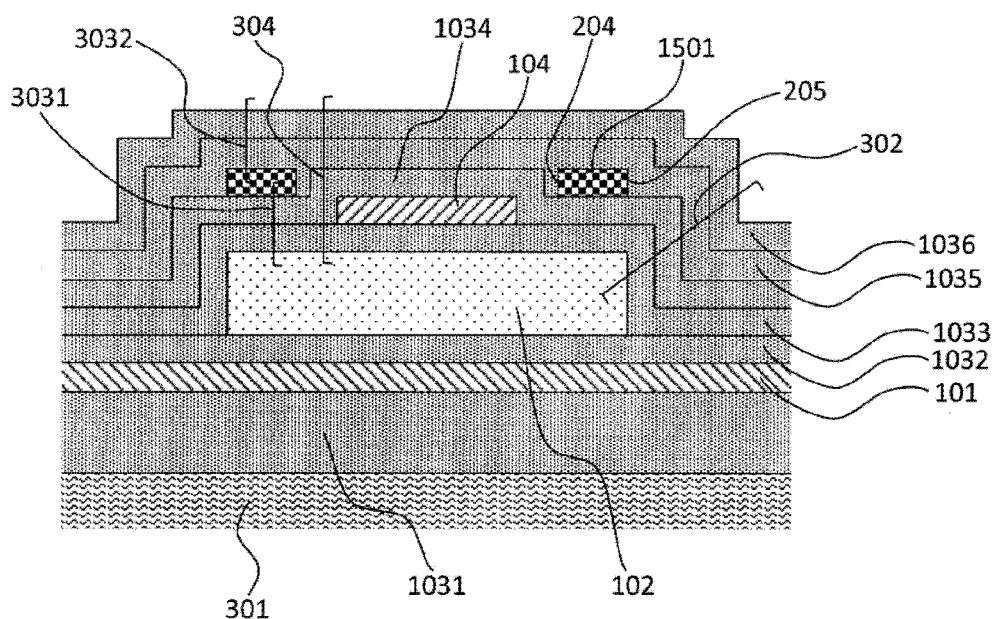
FIG. 17(a) is a cross-sectional view taken along line C-Ce of FIG. 16(b)
FIG. 17(b) is a cross-sectional view taken along line D-D of FIG. 16(b).
Figure 17:
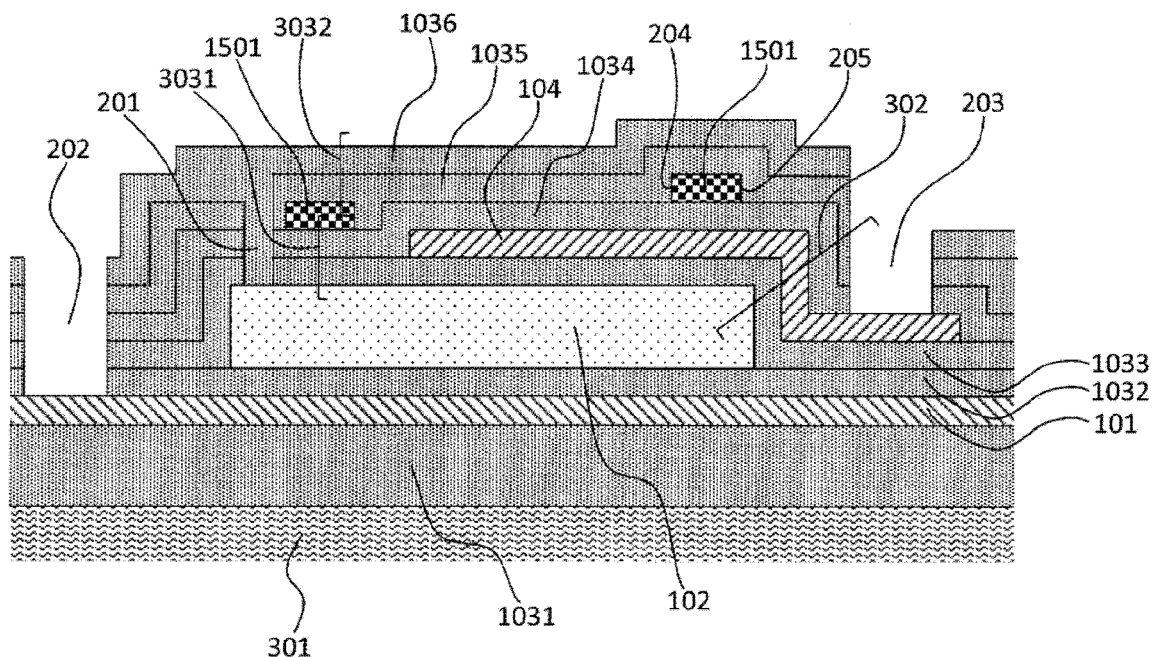

FIG. 16(b) is a top view illustrating an inner configuration of an ultrasonic transducer (CMUT) element in a second embodiment in which the insulating film is removed and the profiles of the cavity layer and a flexible member layer are depicted by the contour lines. In the second embodiment, a flexible member 1501 is provided instead of the region of the second cavity layer surrounded by the contour lines 204 and 205 in the first embodiment. FIG. 17(a) is a cross-sectional view of the CMUT element taken along line C-C' of FIG. 16(b). FIG. 17(b) is a cross-sectional view taken along line D-D' of FIG. 16(b).

As illustrated in FIGS. 17(a) and 17(b), the flexible member 1501 fills in the region which has been described as being made of the second cavity layer 305 in the first embodiment. Such configurations have the same effect as that of the second cavity layer as described in the first embodiment, and the first and second connection portions 3031 and 3032 separated by the flexible member layer are deformed like the parallel link mechanism, so that the bending of the movable portion 304 can be suppressed, which is desirable to increase the vibration area to be equal to or more than a predetermined amplitude ratio of the membrane.

In the manufacturing process of the CMUT element of the first embodiment, breaking and peeling occur in the insulating films 1035 and 1036 of the upper layer of the second cavity layer 305. Therefore, there is a possibility to lower the yield when the CMUT devices are finished. On the other hand, like the second embodiment, the region for the second cavity layer 305 is filled with the flexible member 1501 in the first embodiment, so that it is possible to suppress the insulating films 1035 and 1036 of the upper layer of the flexible member 1501 from being broken and peeled. In this case, it is preferable that the rigidity (Young's modulus) of the flexible member 1501 is close as that of the cavity, and a material may be employed which has a Young's modulus smaller than those of the insulating films of the connection portions 3031 and 3032, the movable portion 304, and the fixing portion 302. Specifically, an organic material such as polyimide having about 1/10 times of the Young's modulus of the insulating film is preferable.

In addition, the method of manufacturing the flexible member layer 1501 of the second embodiment does not need to perform the wet etching using the sacrifice layer, so that there is no connection with the wet etching hole 201.

Third Embodiment

Figure 18:
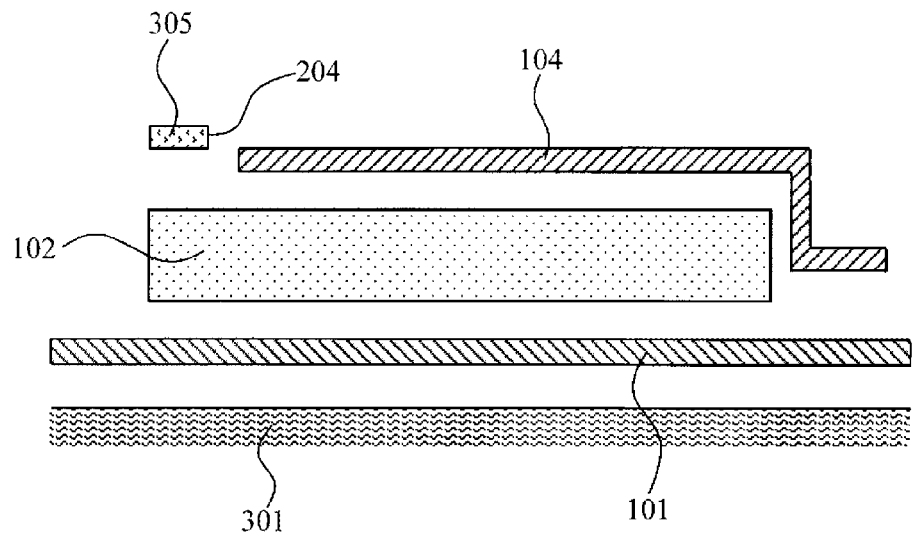
FIG. 18(a) is a cross-sectional view illustrating a CMUT element in a third embodiment of the invention excepting an insulating film.
FIG. 18(b) is a top view when viewed from the upper surface of the substrate.
Figure 18:
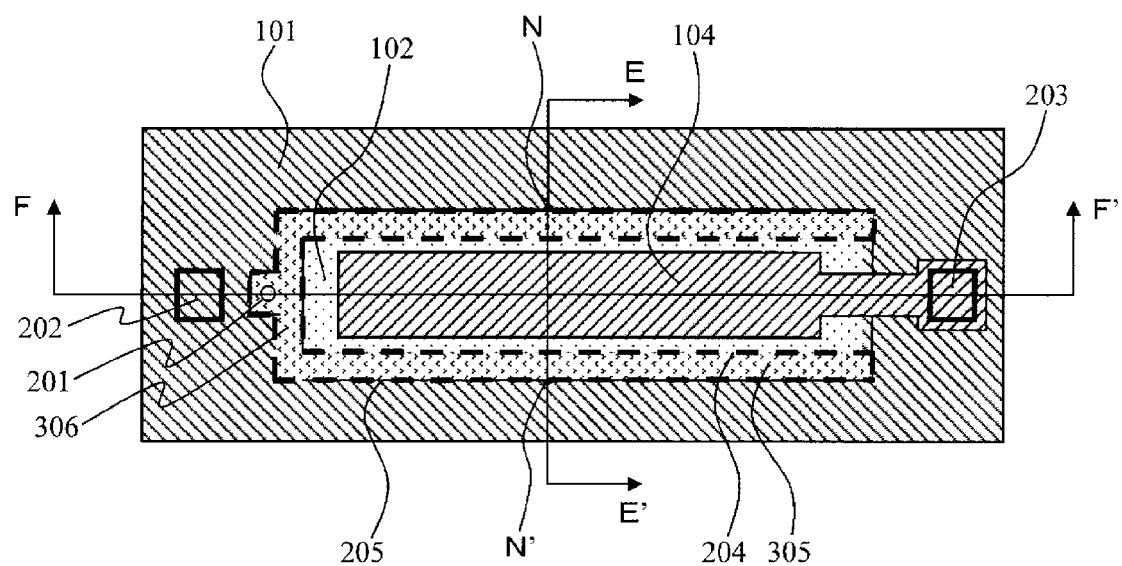
Figure 19:
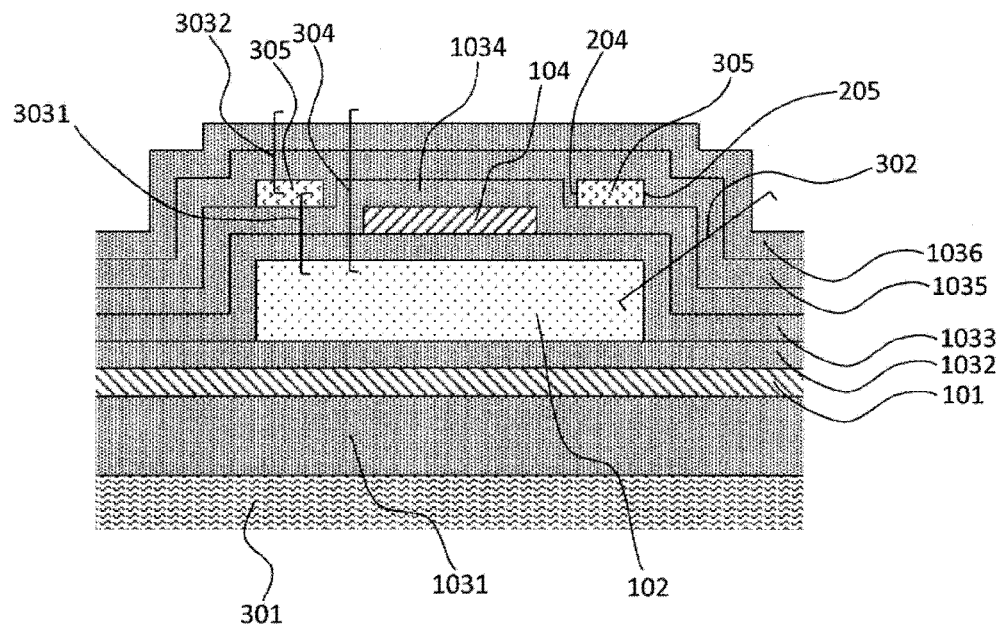
FIG. 19(a) is a cross-sectional view taken along line E-E' of FIG. 18(b)
FIG. 19(b) is a cross-sectional view taken along line F-F' of FIG. 18(b).
Figure 19:
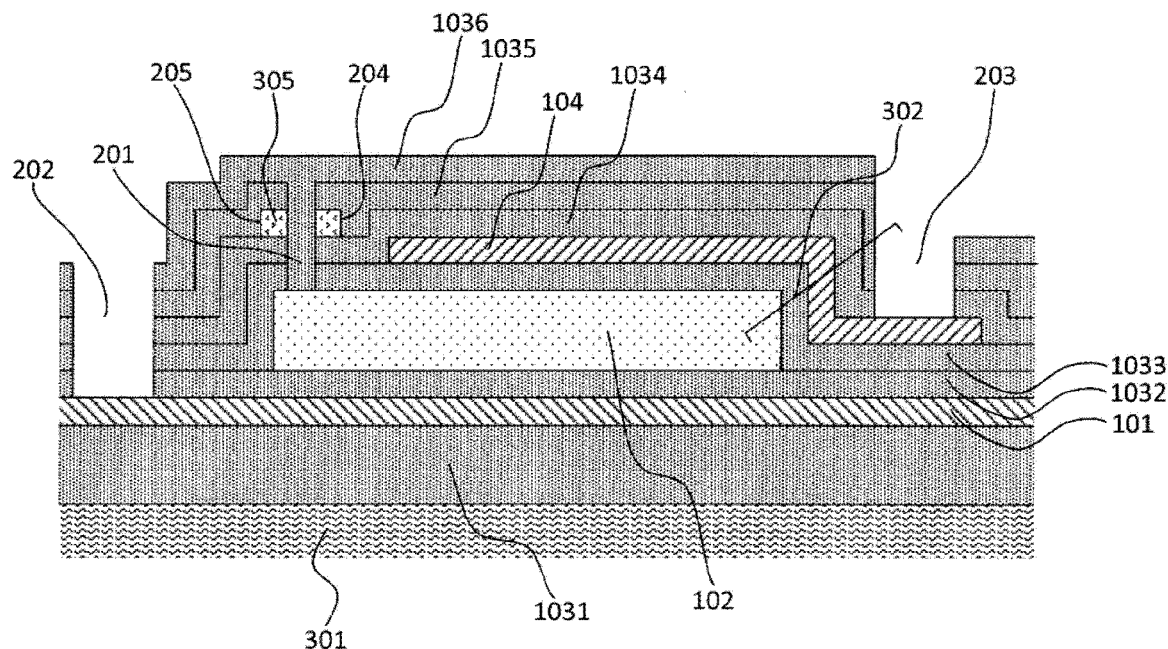

FIG. 18 is a top view illustrating an inner configuration of an ultrasonic transducer (CMUT) element in a third embodiment in which an insulating film is removed and a profile of a cavity layer is depicted by a contour line. The third embodiment has a structure in which the second cavity layer 305 is provided in the region surrounded by the contour lines 204 and 205 similarly to the first embodiment. FIG. 19(a) is a cross-sectional view taken along line E-E' of FIG. 18(b). FIG. 19(b) is a cross-sectional view taken along line F-F' of FIG. 18(b).

The feature of the CMUT element of the third embodiment is that two rows of the second cavity layers 305 are provided with the upper electrode 104 interposed therebetween only in the longitudinal direction of the first cavity layer 102 having a rectangular shape when viewed from the upper surface, and the movable portion 304 of the membrane is supported by the first connection portion 3031 and the second connection portion 3032 formed to be separated by the second cavity layer 305 disposed in parallel.

In a case where the first cavity layer 102 has a rectangular shape, the fixing portion regulating the vibration of the movable portion 304 is a fixing portion of both side surfaces in the longitudinal direction of the first cavity layer 102, so that if the second cavity layer is provided only in that portion, the connection portions 3031 and 3032 are deformed, and the bending of the movable portion 304 can be suppressed. Therefore, it is possible to increase the vibration area to be equal to or more than a predetermined amplitude ratio of the membrane.

Figure 3:
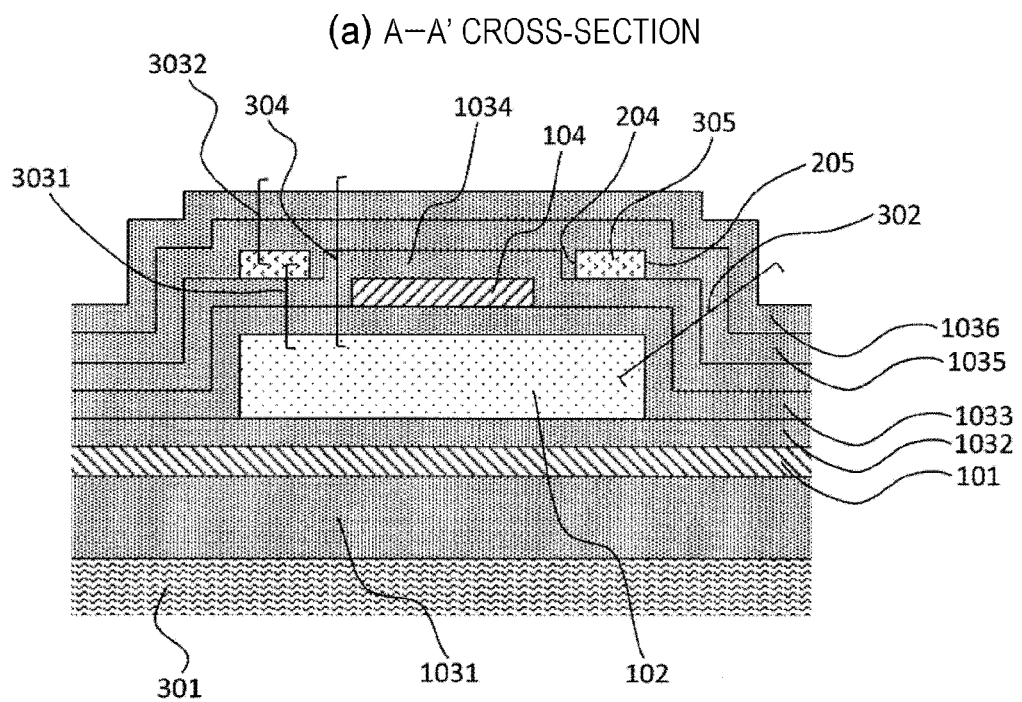
FIG. 3(a) is a cross-sectional view taken along line A-A' of FIG. 2(b)
FIG. 3(b) is a cross-sectional view taken along line B-B' of FIG. 2(b).
Figure 3:
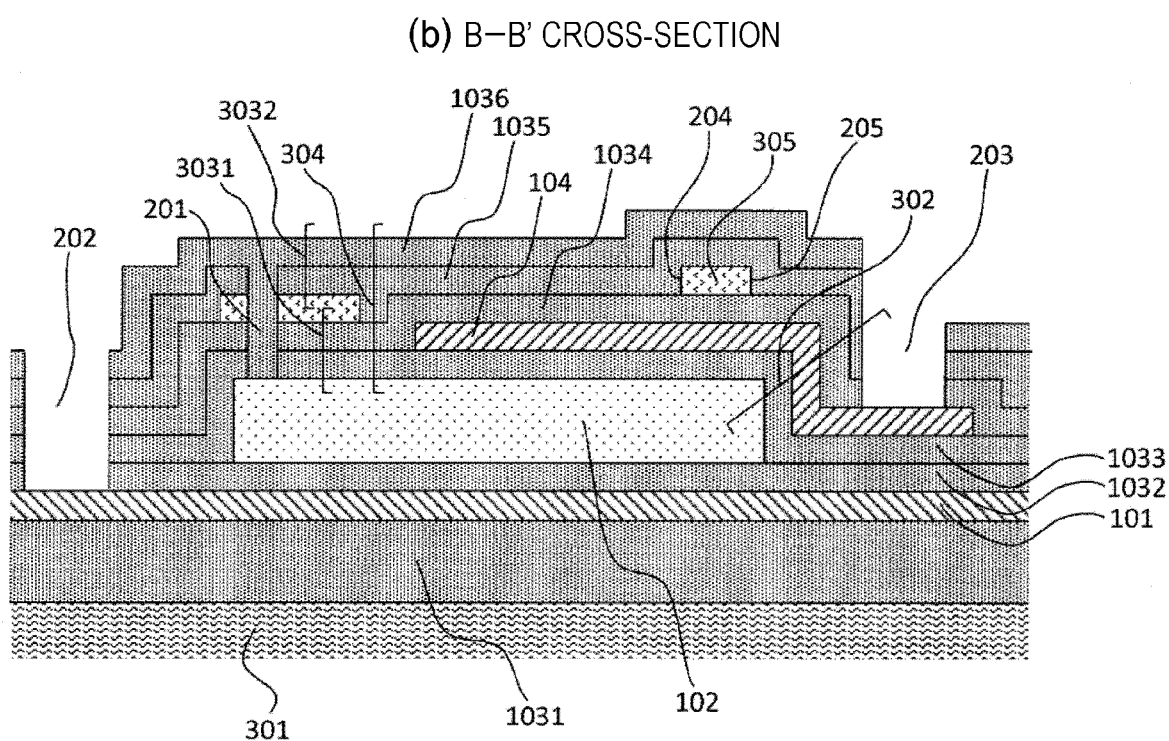
Figure 4:
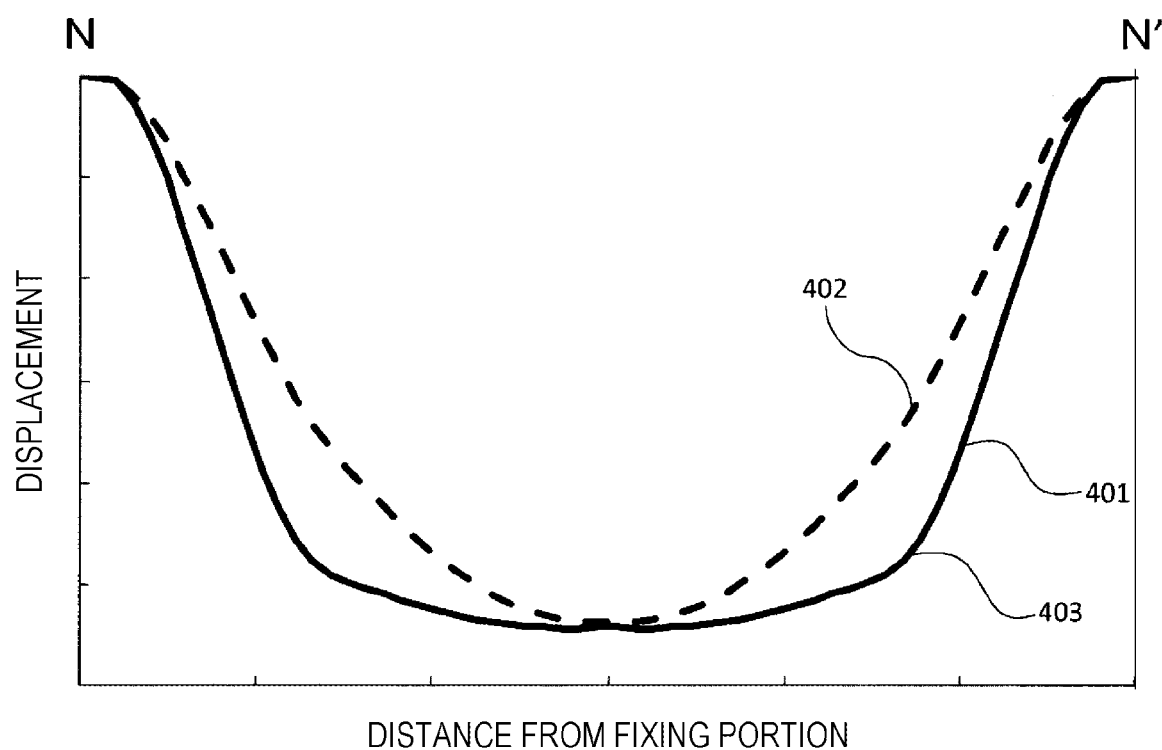
FIG. 4 is a graph comparing displacement shapes of the membrane in cases where a voltage is applied to the first embodiment of the invention and the conventional CMUT.
Figure 5:
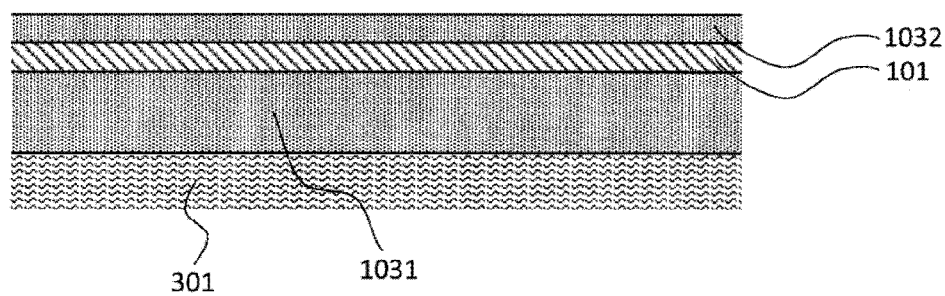
FIG. 5(a) is a cross-sectional view illustrating a manufacturing process of the CMUT element in the cross-section taken along line A-A' of FIG. 2(b)
FIG. 5(b) is a cross-sectional view illustrating a manufacturing procedure of the CMUT element in the cross-section taken along line B-B' of FIG. 2(b).
Figure 5:
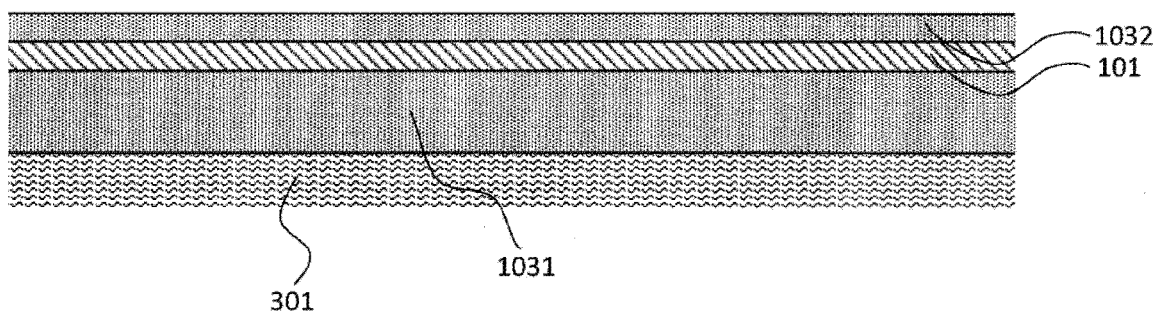
Figure 6:
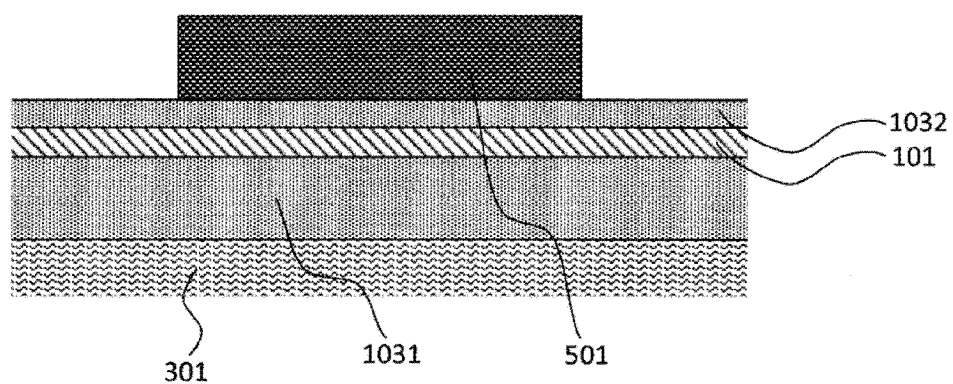
FIG. 6 is a cross-sectional view illustrating a manufacturing procedure of the CMUT element subsequent to FIG. 5.
Figure 6:
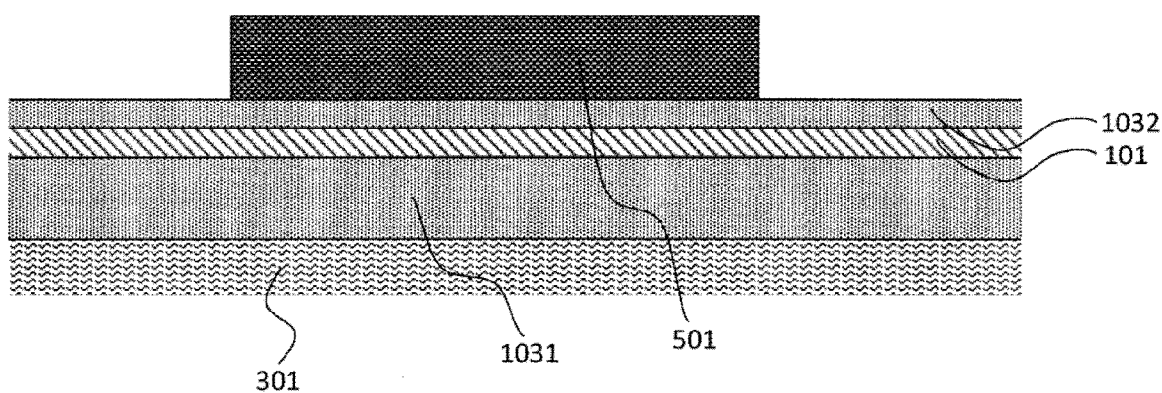
Figure 7:
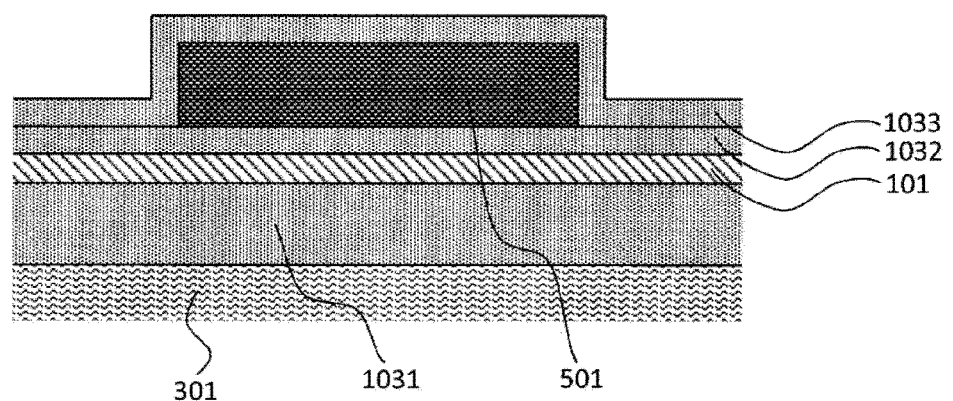
FIG. 7 is a cross-sectional view illustrating a manufacturing procedure of the CMUT element subsequent to FIG. 6.
Figure 7:
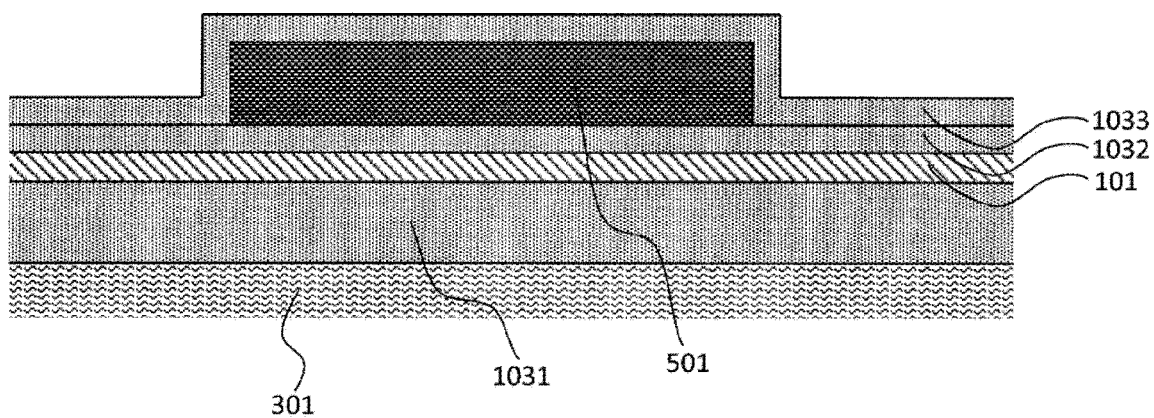
Figure 8:
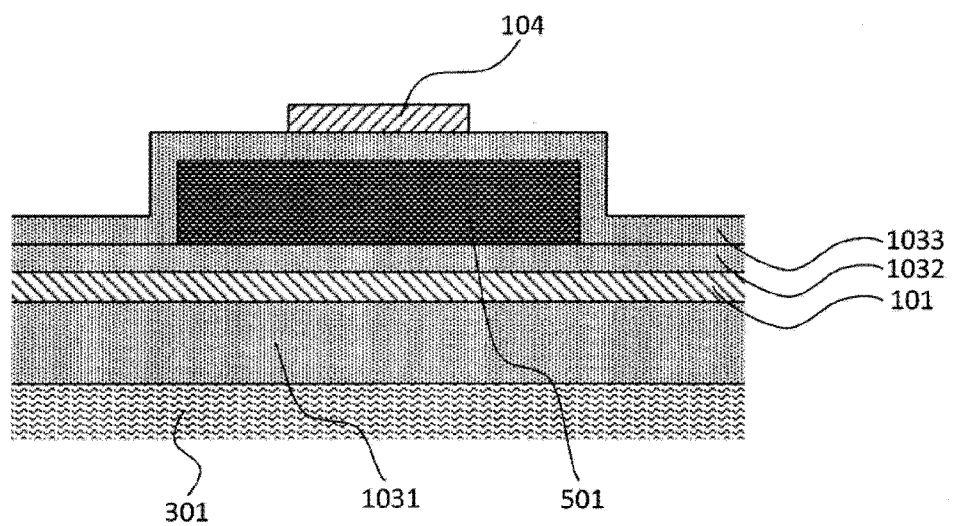
FIG. 8 is a cross-sectional view illustrating a manufacturing procedure of the CMUT element subsequent to FIG. 7.
Figure 8:
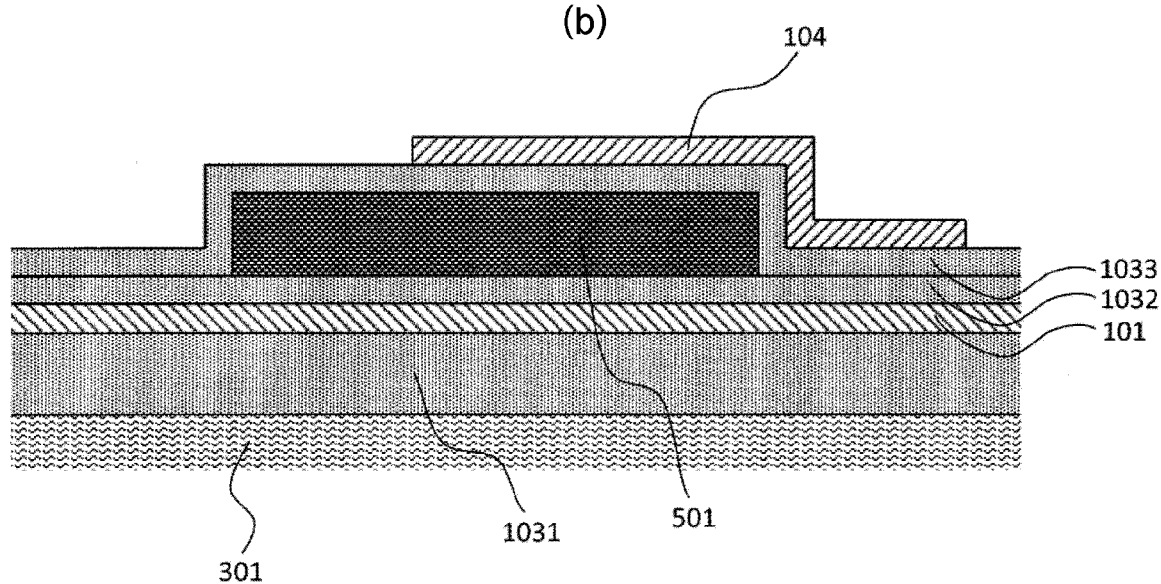
Figure 9:
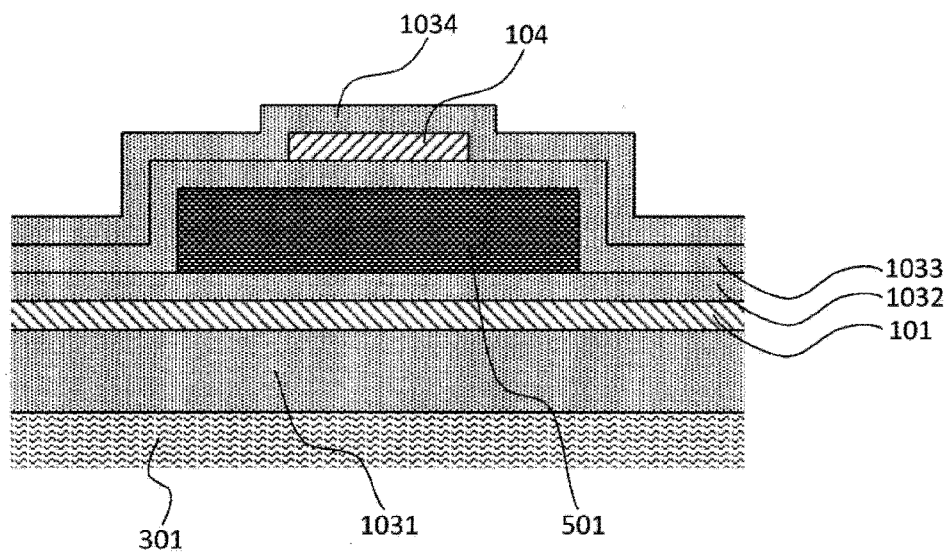
FIG. 9 is a cross-sectional view illustrating a manufacturing view of the CMUT element subsequent to FIG. 8.
Figure 9:
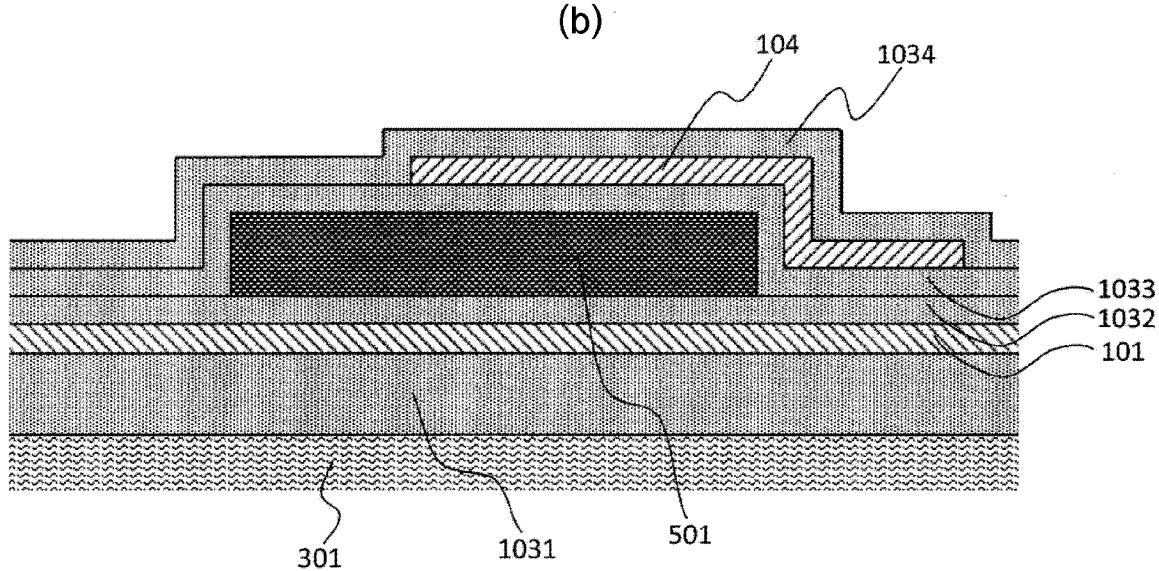
Figure 10:
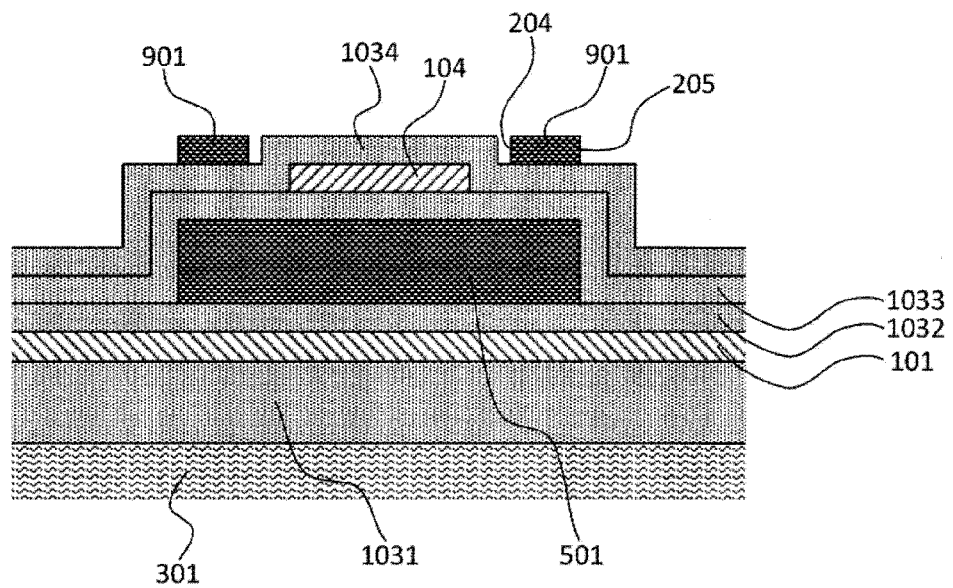
FIG. 10 is a cross-sectional view illustrating a manufacturing view of the CMUT element subsequent to FIG. 9.
Figure 10:
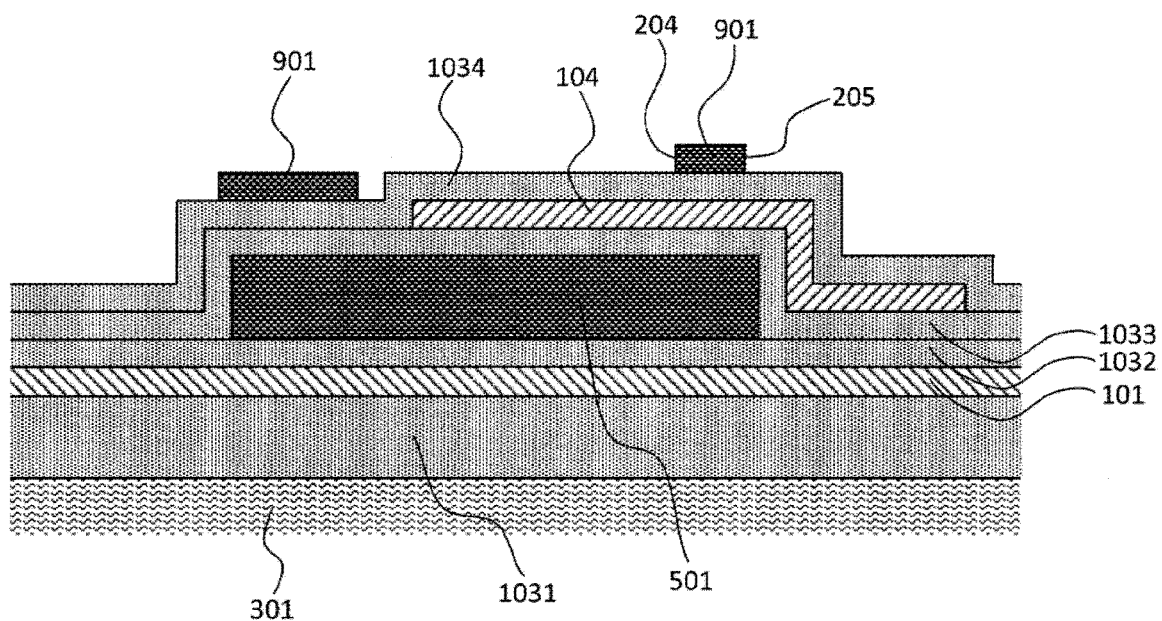
Figure 11:
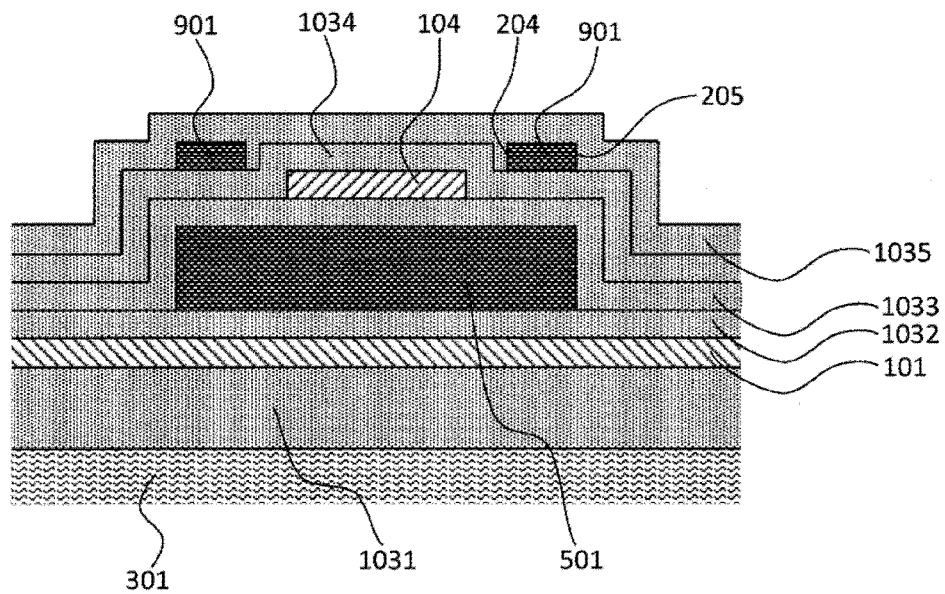
FIG. 11 is a cross-sectional view illustrating a manufacturing procedure of the CMUT element subsequent to FIG. 10.
Figure 11:
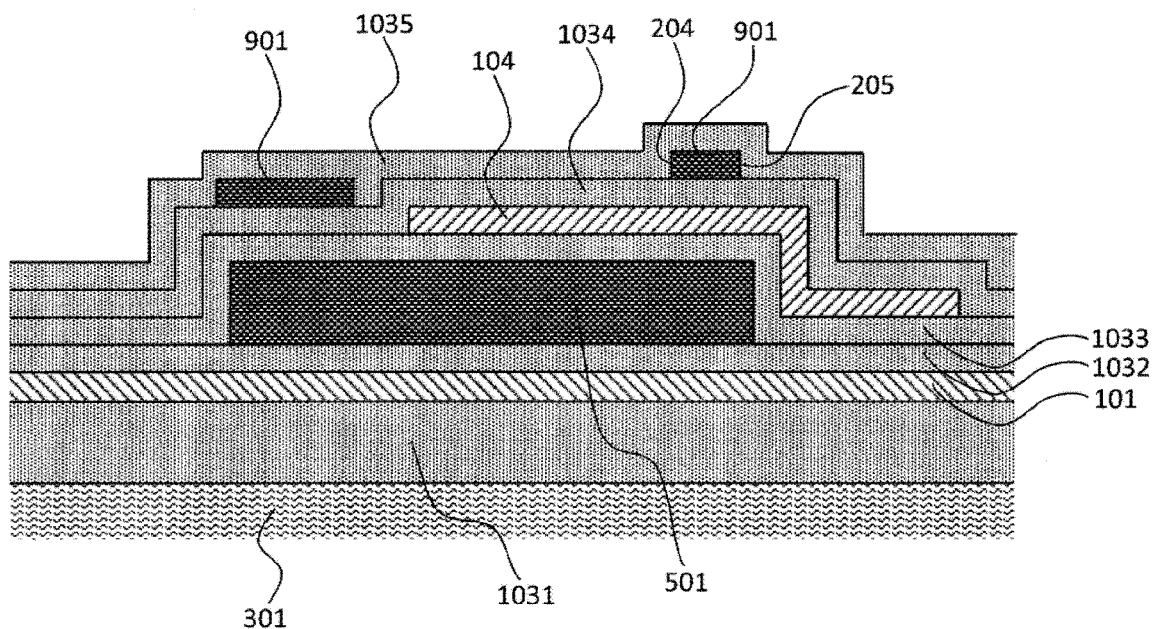
Figure 12:
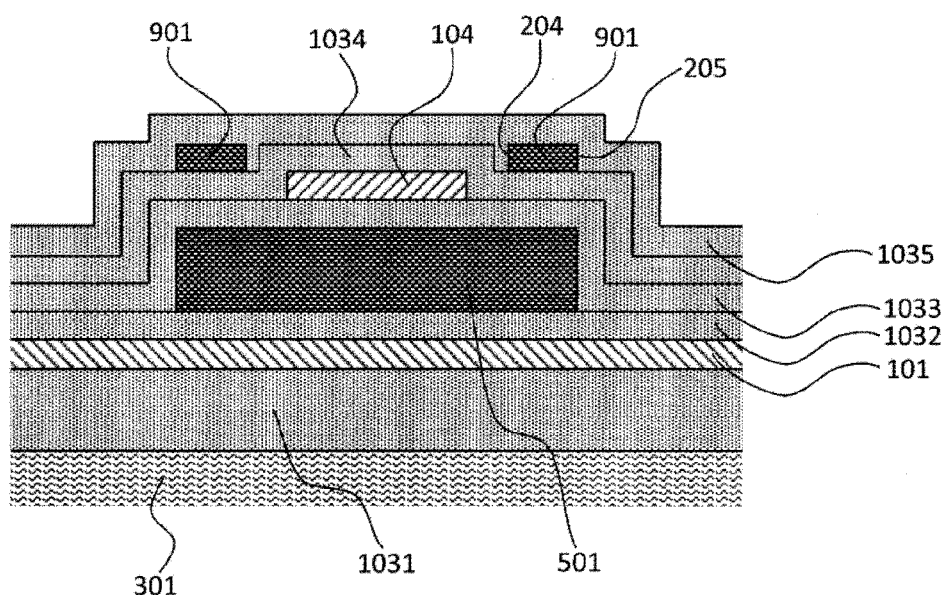
FIG. 12 is a cross-sectional view illustrating a manufacturing procedure of the CMUT element subsequent to FIG. 11.
Figure 12:
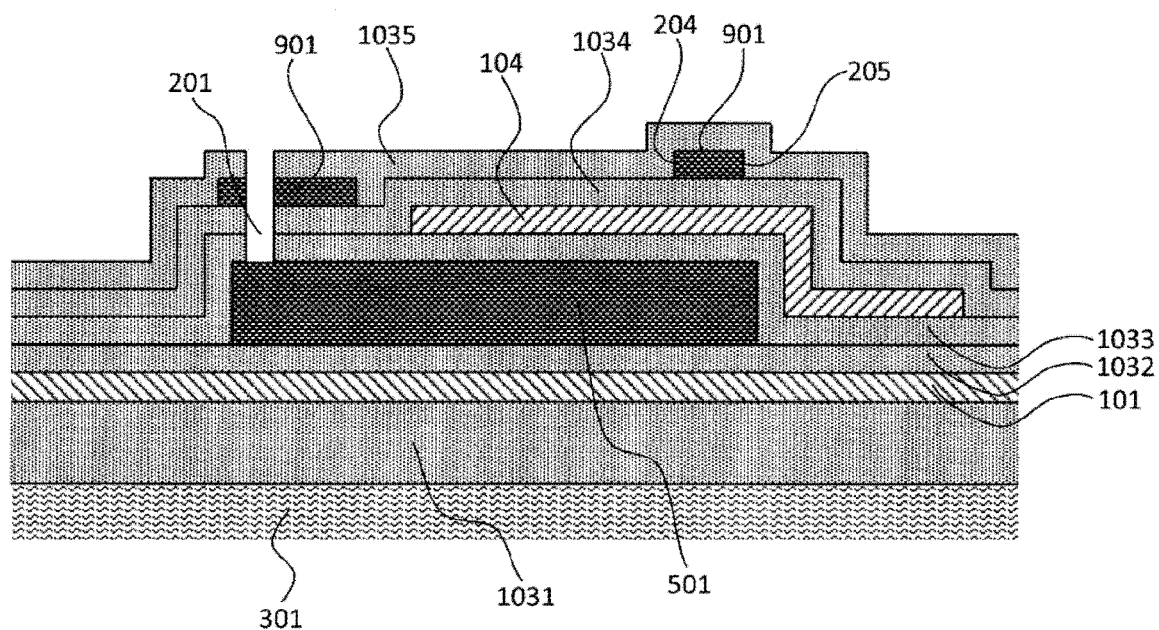
Figure 13:
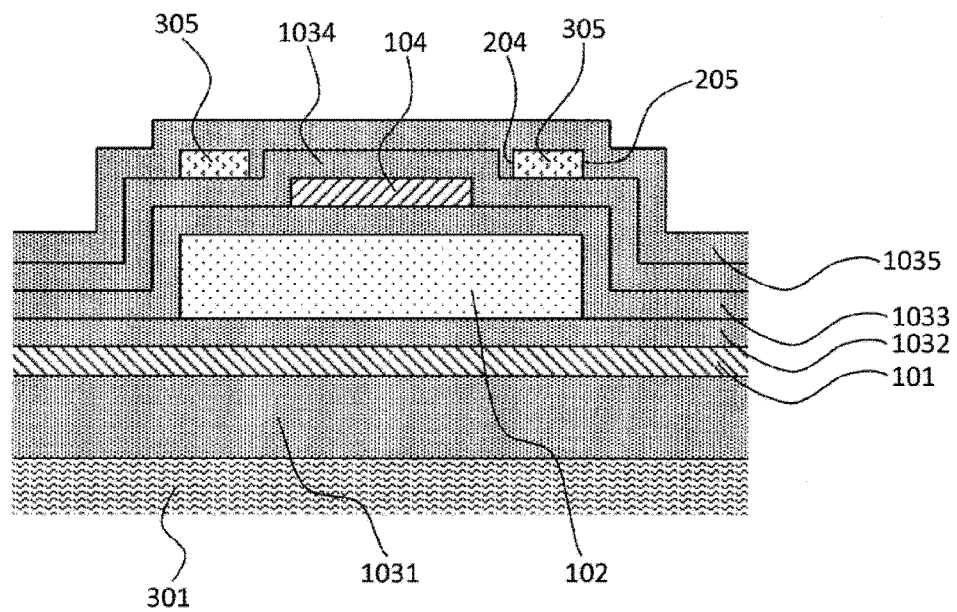
FIG. 13 is a cross-sectional view illustrating a manufacturing procedure of the CMUT element subsequent to FIG. 12.
Figure 13:
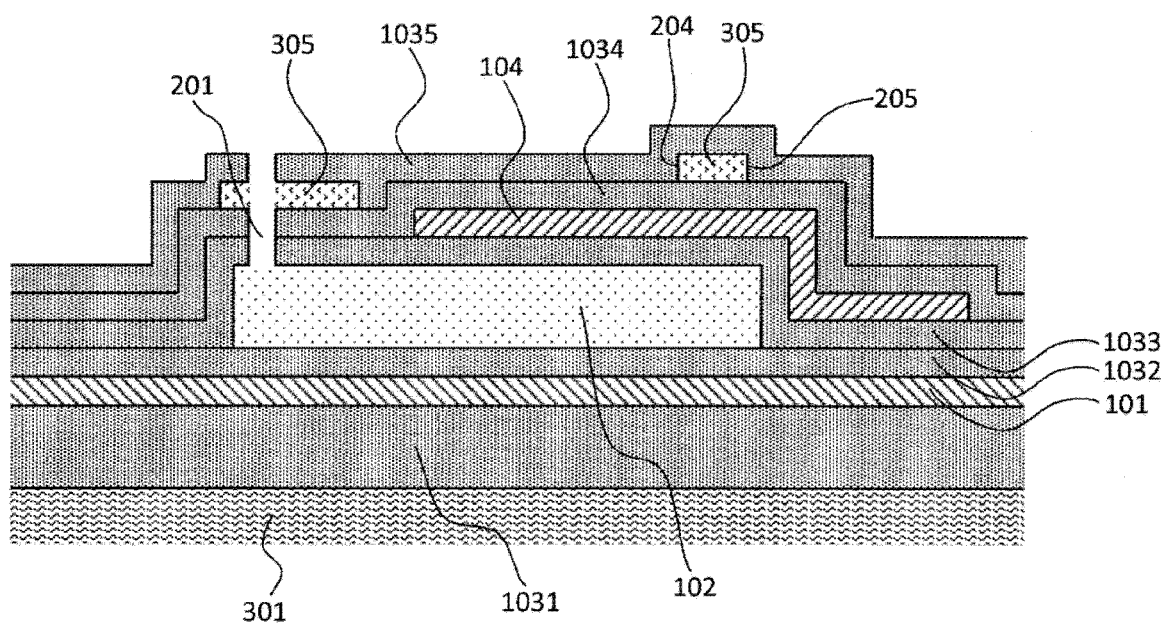
Figure 14:
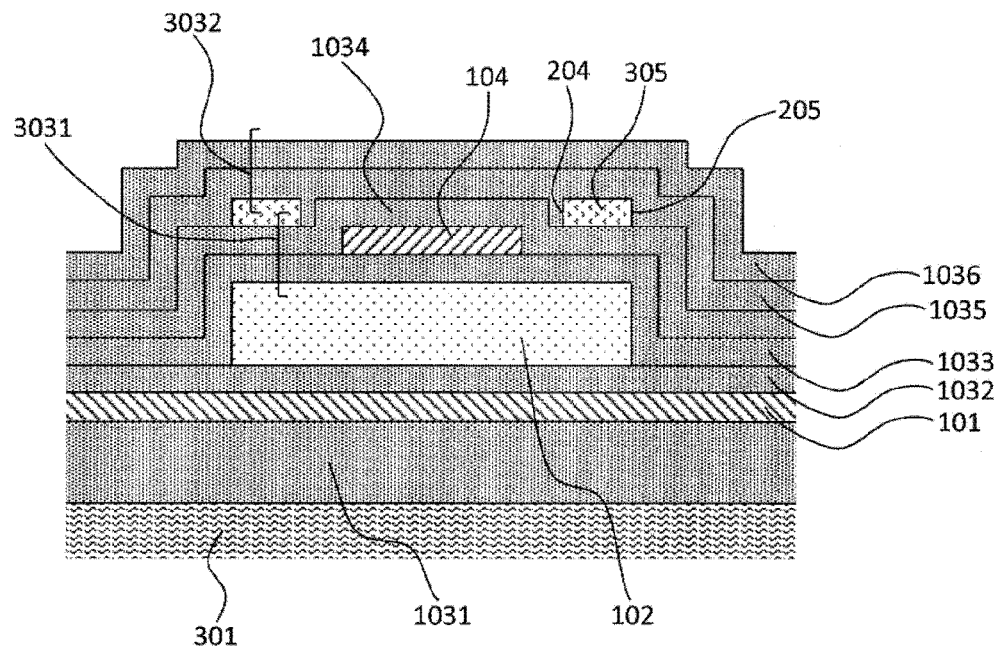
FIG. 14 is a cross-sectional view illustrating a manufacturing procedure of the CMUT element subsequent to FIG. 13.
Figure 14:
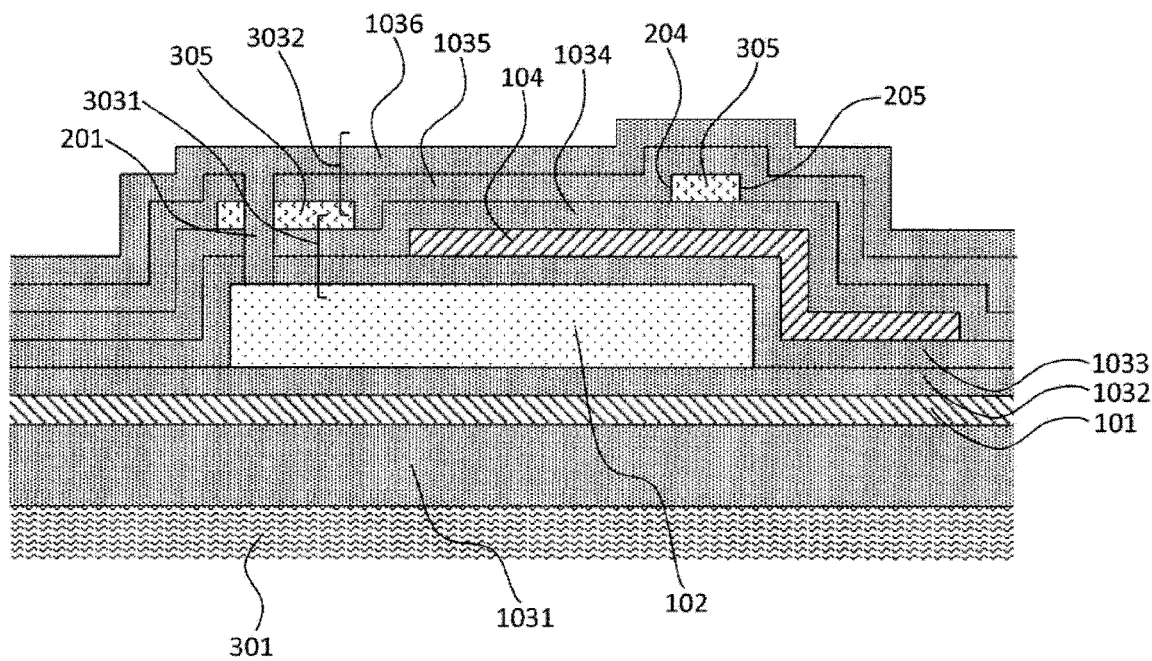
Figure 15:
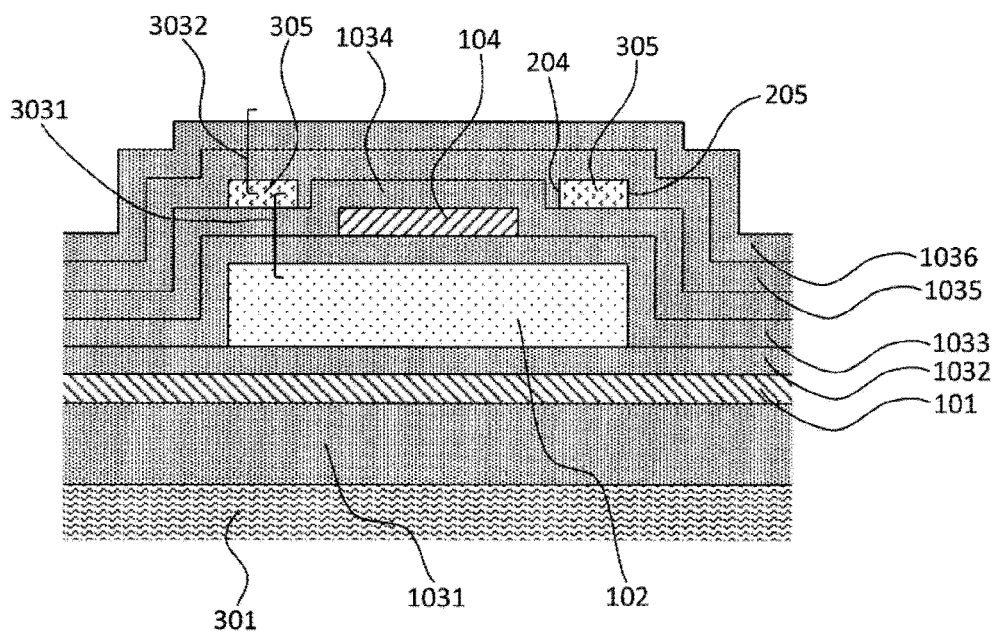
FIG. 15 is a cross-sectional view illustrating a manufacturing procedure of the CMUT element subsequent to FIG. 14.
Figure 15:
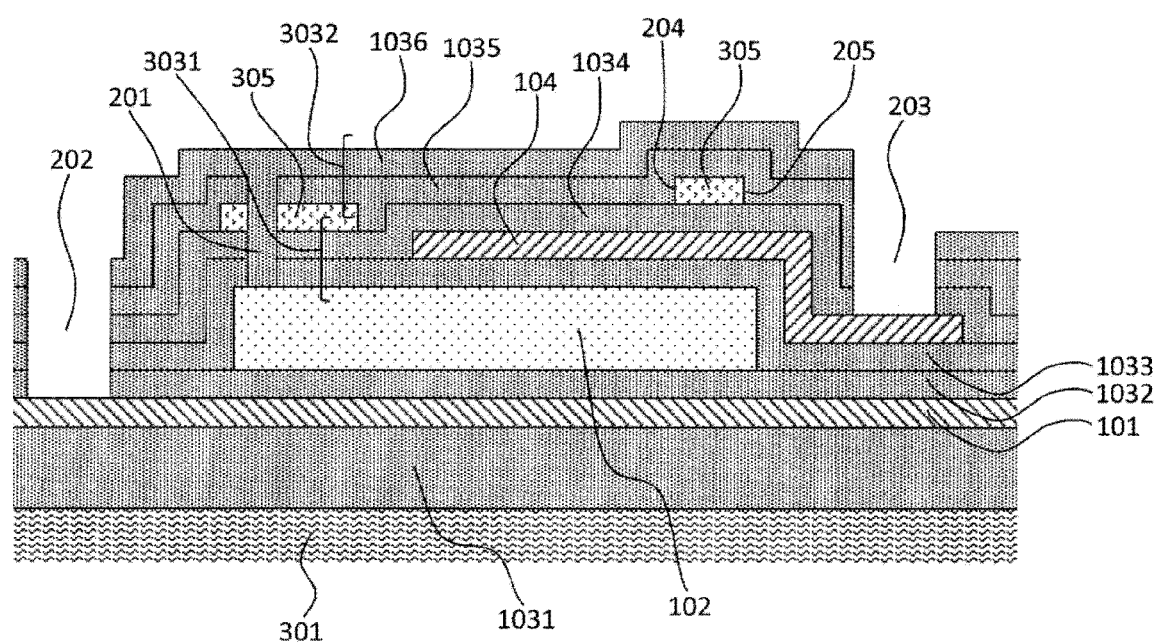

In addition, as illustrated in FIG. 3, in a case where the outer periphery of the first cavity layer 102 is surrounded by the second cavity layer 305 as in the first embodiment, the second cavity layer comes to be provided also in the upper portion of a lead-out line of the upper electrode 104. With such a configuration, film thicknesses of the connection portions 3031 and 3032 of the upper and lower regions of the second cavity layer of the upper portion of the lead-out line lose a balance only by the upper electrode 104, and thus there is a possibility to generate unnecessary vibration when the membrane vibrates. On the other hand, with the configuration described in the third embodiment, as illustrated in FIGS. 19(a) and 19(b), it is possible to suppress that unnecessary vibration is generated when the membrane vibrates without providing the second cavity layer 305 in the upper portion of the lead-out line of the upper electrode 104. However, in a case where the first cavity layer has a rotationally symmetric shape such as a circular shape or a regular hexagon, it is a matter of course that the configuration described in the first embodiment is suitable. In the third embodiment, two rows of the second cavity layers 305 are provided in the longitudinal direction of the first cavity layer 102, and there is provided a second cavity layer 306 which connects two rows of the second cavity layers 305 in order to connect the wet etching hole 201.

In addition, it is also clear that the second cavity layer may be filled with a flexible material by combining the third embodiment and the above-described second embodiment. Further, the second and third embodiments are also described about an example that the flexible member layer 1501 or the contour line 205 of the outer periphery of the second cavity layer 305 is substantially matched with the contour of the profile of the first cavity layer 102. However, there is no need to match these contours, and the contour line may be positioned outside or inside as long as it is disposed in the vicinity of the contour of the profile of the first cavity layer 102.

Note that the flexible member layer 1501 or the contour line 204 of the inner periphery of the second cavity layer 305 is necessarily positioned inside the contour of the profile of the first cavity layer 102 when viewed from the upper surface of the first cavity layer 102.

Finally, a configuration example and functions of the ultrasonic image pickup device which includes the CMUT element of the above-described embodiments will be described with reference to FIGS. 20 and 21.

First, the configuration of the ultrasonic image pickup device of the embodiment will be described with reference to FIGS. 20 and 21. FIG. 20 is a perspective view illustrating the entire configuration of the ultrasonic image pickup device, and FIG. 21 is a block diagram illustrating the functions of the ultrasonic image pickup device.

Figure 20:
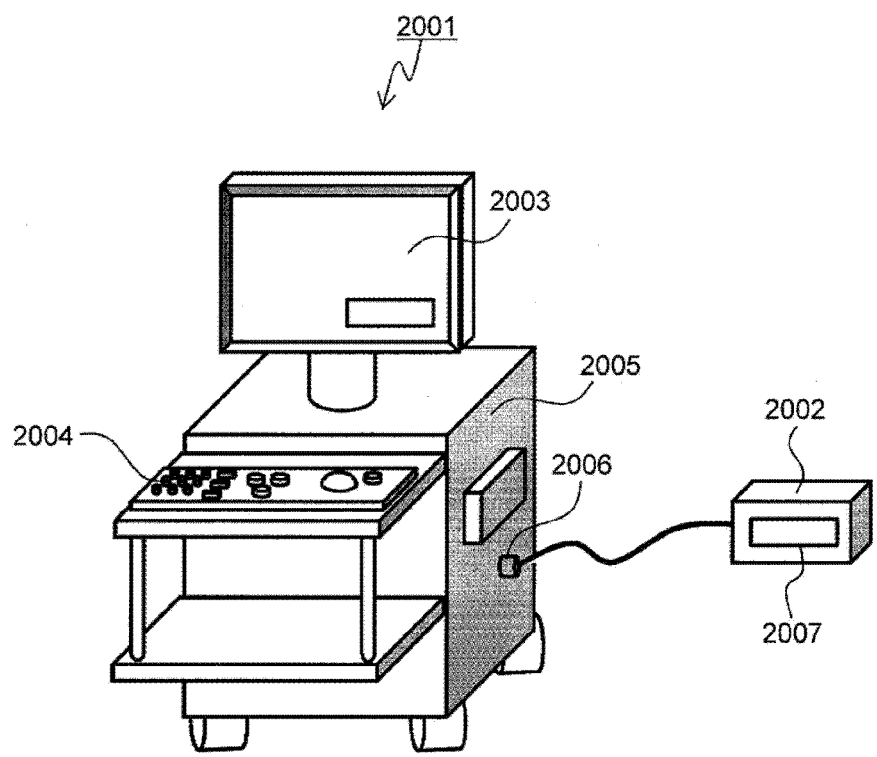
FIG. 20 is a perspective view illustrating the entire configuration of an ultrasonic image pickup device to which the invention is applied.

As illustrated in FIG. 20, the ultrasonic image pickup device 2001 includes a main body 2005 which stores the ultrasonic transceiver circuit which transceives ultrasonic wave, and a signal processing circuit which processes an echo signal received by an ultrasonic transceiver circuit and generates an ultrasonic image of an inspection target, a display 2003 which is connected to the main body 2005 and displays a GUI to interface with the ultrasonic image and an operator, an operation unit 2004 which is used by the operator, and an ultrasonic probe 2002 which is connected to the ultrasonic transceiver circuit through a connection portion 2006 fixed to the main body 2005.

The ultrasonic probe 2002 is a device which comes into contact with an object and transceives ultrasonic waves with the object, and includes an ultrasonic transducer 2007 in which a number of transducer elements are arranged in a one-dimensional or two-dimensional array, an acoustic lens, and a backing material. In the ultrasonic image pickup device of the embodiment, the ultrasonic transducer 2007 is, for example, configured by several hundreds to about ten thousands of CMT elements which are arranged in a one-dimensional or two-dimensional array.

Further, FIG. 20 illustrates a movable ultrasonic image pickup device as an example which includes wheels in the bottom of the main body 2005, but the embodiment is able to be applied to an ultrasonic image pickup device fixed in an inspection room, a portable ultrasonic image pickup device of a note-type or a box-type, and other ultrasonic image pickup devices disclosed in public.

Figure 21:
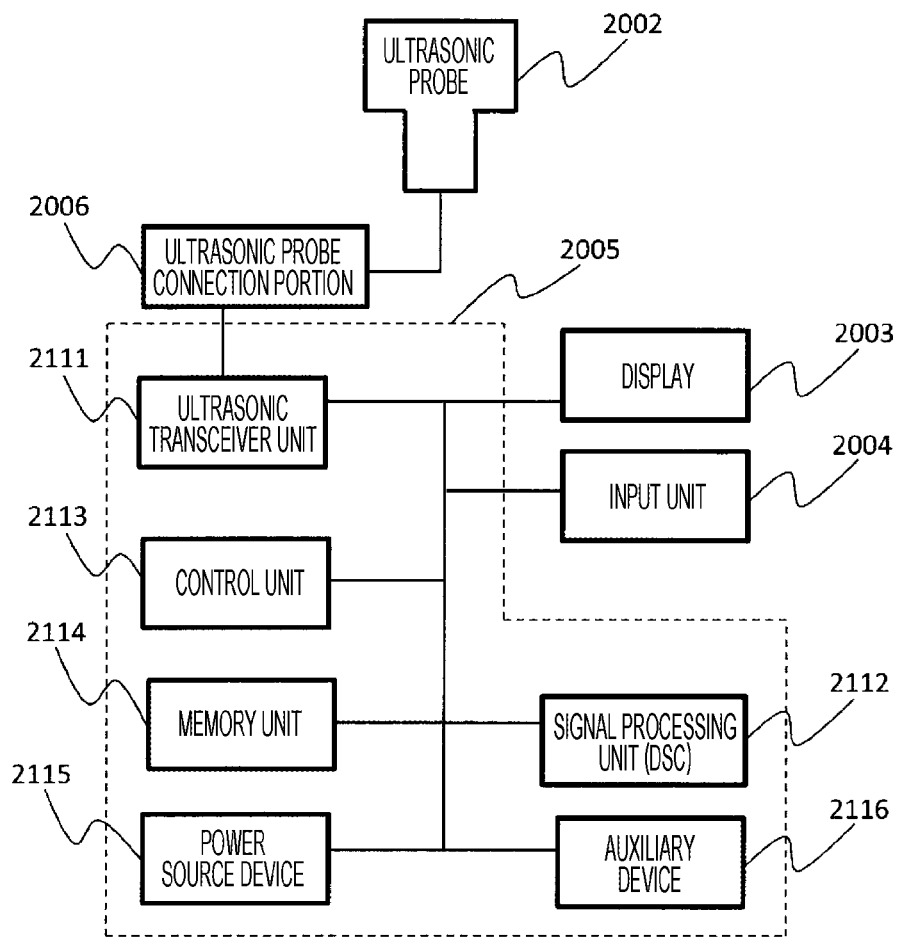
FIG. 21 is a functional block diagram of the ultrasonic image pickup device to which the invention is applied.

As illustrated in FIG. 21, the main body 2005 includes an ultrasonic transceiver circuit 2111, a signal processing circuit 2112, a control unit 2113, a memory unit 2114, a power source device 2115, and an auxiliary device 2116.

The ultrasonic transceiver circuit 2111 generates a drive voltage to transmit ultrasonic waves from the ultrasonic probe 2002 and to receive an echo signal from the ultrasonic probe 2002, and includes a delay circuit, a filter, and a gain adjusting circuit.

The signal processing circuit 2112 performs a correction such as a LOG compression and a depth correction, and a process necessary for creating an image on the received echo signal, and may include a DSC (digital scan converter), a color doppler circuit, and an FFT analysis unit. As the signal processing of the signal processing circuit 2112, analog signal processing and digital signal processing both can be performed, and some part may be realized by software or may be realized by an ASIC (application specific integrated circuit) or an FPGA (field-programmable gate array). A marked-up copy of the Substitute Specification indicating changes is also enclosed.

The control unit 2113 controls devices which are connected to the respective circuits of the main body 2005 and the main body 2005. The memory unit 2114 stores information and parameters necessary for the signal processing and the control, and the processing results. The power source device 2115 supplies necessary power to the respective portions of the ultrasonic image pickup device. The auxiliary device 2116 is used to realize additional functions of the ultrasonic image pickup device (for example, sound generation) besides the above-described respective units, and is appropriately added as needed.

Further, the invention is not limited to the above embodiments, and various modifications can be made. For example, the embodiments are described in a clearly understandable way for the invention, and the invention is not necessarily to provide all the configurations described above. In addition, some configurations of a certain embodiment may be replaced with the configurations of another embodiment, and the configuration of the other embodiment may be added to the configuration of a certain embodiment. Furthermore, additions, omissions, and substitutions may be made on some configurations of each embodiment using other configurations.

REFERENCE SIGNS LIST 101 lower electrode
102, 305 cavity layer
103 fixing portion (insulating film)
104 upper electrode
105 membrane
106, 107 insulating film
201 wet etching hole
202 opening to lower electrode
203 opening to upper electrode
204 contour line of second cavity layer serving as boundary surrounding movable portion
205 contour line of second cavity layer serving as boundary surrounding connection portion
301 substrate
302 fixing portion
3031, 3032 connection portion
304 movable portion
305 second cavity layer 306 second cavity layer for two rows of connecting second cavity layers in third embodiment
401 displacement shape of first embodiment when voltage is applied
402 displacement shape of conventional CMUT when voltage is applied
403 curve of displacement shape of first embodiment
501 sacrifice layer
1031, 1032, 1033, 1034, 1035, 1036 insulating film
1501 flexible member
2001 ultrasonic image pickup device
2002 ultrasonic probe
2003 display
2004 operation unit
2005 main body
2006 probe connection portion
2007 ultrasonic transducer
2111 ultrasonic transceiver unit
2112 signal processing unit
2113 control unit
2114 memory unit
2115 power source device
2116 auxiliary device

The invention claimed is:

1. An ultrasonic transducer element, comprising:
a substrate;
a lower electrode which is formed on a first principal surface of the substrate;
a first insulating film which is formed on the lower electrode;
a first cavity layer which is formed on the first insulating film;
a second insulating film which is formed on the first cavity layer;
an upper electrode which is formed on the second insulating film and disposed at a position overlapping with the first cavity layer when viewed from an upper surface;
a third insulating film which is formed on the upper electrode;
a second cavity layer which is formed on the third insulating film;
a fourth insulating film which is formed on the second cavity layer;
when viewed from an upper surface of the first principal surface of the substrate,
a fixing portion which is configured by the second, third, and fourth insulating films surrounding an outer periphery of the first cavity layer;
a movable portion which is configured by a region inside the second cavity layer in a membrane, the membrane being configured by the second, third, and fourth insulating films and the upper electrode formed on the first cavity layer; and
a first connection portion and a second connection portion which is stacked with a gap with the first connection portion, the connection portions being configured by the second, third, and fourth insulating films connecting the movable portion and the fixing portion.

2. The ultrasonic transducer element according to claim 1, wherein the second cavity layer is provided between the first connection portion and the second connection portion.

3. The ultrasonic transducer element according to claim 1, wherein a material layer having an elastic modulus lower than the insulating film is formed on the third insulating film instead of the second cavity layer, wherein the movable portion becomes a region inside the material layer having a low elastic modulus instead of the second cavity layer in the membrane, and
wherein the material layer having the low elastic modulus is included between the first connection portion and the second connection portion compared to both the connection portions.

4. The ultrasonic transducer element according to claim 2, wherein the second cavity layer or a material layer having a low elastic modulus compared to both of the first connection portion and the second connection portion is disposed at a continuous position bordering an outer periphery of the first cavity layer and at a position overlapping with the first cavity layer when viewed from the upper surface of the first principal surface of the substrate.

5. The ultrasonic transducer element according to claim 2, wherein the second cavity layer or a material layer having a low elastic modulus compared to both of the first connection portion and the second connection portion is disposed at a position bordering at least two rows of outer peripheries which are continuous in a belt shape along two sides facing the first cavity layer when viewed from the upper surface of the first principal surface of the substrate, and at a position overlapping with the first cavity layer.

6. The ultrasonic transducer element according to claim 2, wherein the second cavity layer or a material layer having a low elastic modulus compared to both of the first connection portion and the second connection portion is disposed such that an inner periphery thereof is disposed at a position overlapping with the first cavity layer compared to the first cavity layer, and part or all of an outer periphery thereof is disposed in a region outside a contour of a profile of the first cavity layer when viewed from the upper surface of the first principal surface of the substrate.

7. The ultrasonic transducer element according to claim 1, wherein a profile shape of the first cavity layer includes a rectangular shape, a circular shape, or a hexagonal shape when viewed from the upper surface of the first principal surface of the substrate.

8. A method of manufacturing an ultrasonic transducer element which is formed in a first principal surface of a substrate, the method comprising:
(a) forming a first electrode on the first principal surface of the substrate;
(b) forming a first insulating film on the electrode;
(c) forming a first sacrifice layer at a position overlapping with the first electrode on the first insulating film when viewed from an upper surface;
(d) forming a second insulating film on the first sacrifice layer;
(e) forming a second electrode at a position which is formed on the second insulating film and overlaps with the first sacrifice layer when viewed from the upper surface;
(f) forming a third insulating film on the second electrode;
(g) forming a second sacrifice layer on the third insulating film to be overlapped with an outer periphery of the first sacrifice layer;
(h) forming a fourth insulating film on the second sacrifice layer and the third insulating film;
(i) forming an opening which passes through the fourth insulating film, the second sacrifice layer, the third insulating film, and the second insulating film, and reaches the first sacrifice layer;

(j) forming first and second cavity layers by removing the first and second sacrifice layers through the opening to form a first connection portion between the first cavity layer and the second cavity layer and a second connection portion in an upper portion of the second cavity layer; and (k) forming a fifth insulating film on the fourth insulating film to seal the opening.

9. The method of manufacturing an ultrasonic transducer element according to claim 8, further comprising:

forming a material layer, on the third insulating film, to be overlapped with the outer periphery of the first sacrifice layer, the material layer having a low elastic modulus compared to the third insulating film, instead of (g);

forming a fourth insulating film on the material layer having the low elastic modulus and the third insulating film, instead of (h);

forming an opening which passes through the fourth insulating film, the third insulating film, and the second insulating film and reaches the first sacrifice layer, instead of (i); and forming the first cavity layer by removing the first sacrifice layer through the opening to form the first connection portion between the first cavity layer and the material layer having the low elastic modulus and the second connection portion in the upper portion of the material layer having the low elastic modulus, instead of (j).

10. An ultrasonic image pickup device, comprising:

an ultrasonic probe which is provided with an ultrasonic transducer in which the ultrasonic transducer elements according to claim 1 are arranged in a one-dimensional array or a two-dimensional array.

* * * * *